United States Patent
Coller et al.

(10) Patent No.: US 10,905,778 B2
(45) Date of Patent: Feb. 2, 2021

(54) METHODS AND COMPOSITIONS FOR TREATING A PREMATURE STOP CODON-MEDIATED DISORDER

(71) Applicant: Case Western Reserve University, Cleveland, OH (US)

(72) Inventors: Jeffery M. Coller, Cleveland, OH (US); Thomas Sweet, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 16/665,526

(22) Filed: Oct. 28, 2019

(65) Prior Publication Data

US 2020/0101174 A1 Apr. 2, 2020

Related U.S. Application Data

(63) Continuation of application No. PCT/US2019/053260, filed on Sep. 26, 2019.

(60) Provisional application No. 62/805,793, filed on Feb. 14, 2019, provisional application No. 62/747,646, filed on Oct. 18, 2018, provisional application No. 62/736,834, filed on Sep. 26, 2018.

(51) Int. Cl.
*A61K 48/00* (2006.01)
*A61P 25/08* (2006.01)

(52) U.S. Cl.
CPC .......... *A61K 48/0066* (2013.01); *A61P 25/08* (2018.01)

(58) Field of Classification Search
None
See application file for complete search history.

(56) References Cited

U.S. PATENT DOCUMENTS

2017/0354672 A1* 12/2017 Siegwart .............. A61K 9/0019

FOREIGN PATENT DOCUMENTS

| WO | 2017/049409 A1 | 3/2017 | |
| WO | WO-2017152809 A1* | 9/2017 | ............. A61K 48/00 |

OTHER PUBLICATIONS

Shi et al, Mosaic SCN1A mutations in familial partial epilepsy with antecedent febrile seizures, Genes, Brain and Behavior, 2012, 11: 170-176 (Year: 2012).*
Machine translation of WO 2017/152809 with sequence listing, pp. 1-23 (Year: 2017).*
International Search Report for Patent Application No. PCT/US2019/053260, dated Jan. 30, 2020.

* cited by examiner

*Primary Examiner* — Ekaterina Poliakova-Georgantas
(74) *Attorney, Agent, or Firm* — Tarolli, Sundheim, Covell & Tummino LLP

(57) ABSTRACT

Modified tRNAs can be used to express in a mammalian cell a functional gene product encoded by a gene containing a premature stop codon and/or to treat a disease mediated by a premature stop codon.

6 Claims, 6 Drawing Sheets

Specification includes a Sequence Listing.

| position | residues | ratios | position | residues | ratios |
|---|---|---|---|---|---|
| 0 | Gm/G | 1/4 | 35 | Ψ/U | 7/50 |
| 1 | Ψ/U | 3/14 | 36 | Ψ/xU/U | 23/50 |
| 4 | Am/A | 2/28 | 37 | m¹I/ms²t⁶A/t⁶A/ | 6/2/22/ |
| 4 | Um/U | 6/45 | | m⁶⁶A/i⁶A/xA/A | 2/48/4/45 |
| 4 | Cm/C | 4/51 | 37 | m¹G/o2yW/xG/ | 33/6/2/ |
| 4 | Gm/G | 2/41 | | yW/G | 7/1 |
| 6 | m²G/G | 20/36 | 38 | Ψ/U | 17/1 |
| 7 | m²G/G | 1/69 | 38 | m⁵C/xC/C | 10/1/26 |
| 9 | m¹A/A | 1/69 | 39 | m¹Ψ/Ψ/hu/ | 2/8/ |
| 9 | m¹G/xG/G | 56/1/43 | | Um/Ψ/U | 1/7/92 |
| 10 | m²G/G | 103/70 | 39 | Gm/G | 4/32 |
| 12 | ac⁴C/C | 32/21 | 40 | Ψ/U | 6/1 |
| 13 | Ψ/U | 47/8 | 40 | m⁵C/C | 3/139 |
| 13 | Cm/C | 1/83 | 44 | Um/xU/U | 20/2/18 |
| 14 | m¹A/xA/A | 9/1/165 | e11 | Ψ/U | 2/4 |
| 16 | D/U | 123/25 | e12 | Ψ/U | 8/11 |
| 17 | D/U | 39/0 | e14 | Ψ/U | 2/8 |
| 18 | Gm/G | 40/138 | e2 | m⁵C/C | 7/7 |
| 20 | acp³U/D/U | 4/118/11 | 46 | m⁷G/G | 86/39 |
| 20a | acp³U/D/Ψ/xU/U | 6/64/2/2/2 | 47 | D/xU/U | 83/1/16 |
| 20b | D/Ψ/U | 8/6/2 | 48 | D/U | 1/28 |
| 25 | Ψ/U | 1/28 | 48 | m⁵C/xC/C | 95/1/46 |
| 26 | Ψ/U | 1/24 | 49 | xA/A | 1/19 |
| 26 | m²₂G/m²G/xG/G | 90/16/2/8 | 49 | m⁵C/xC/C | 64/1/13 |
| 27 | Ψ/U | 70/10 | 50 | Ψ/U | 4/45 |
| 27 | m²₂G/G | 3/14 | 50 | m⁵C/C | 15/71 |
| 28 | Ψ/U | 37/38 | 54 | m⁵U/m¹U/Ψ/U | 16/111/11/17 |
| 30 | Ψ/U | 1/4 | 55 | Ψ/U | 166/12 |
| 31 | Ψ/U | 4/2 | 58 | m¹A/xA/A | 151/1/26 |
| 32 | Ψm/Um/Ψ/U | 2/6/24/8 | 64 | Ar(p)A | 2/43 |
| 32 | Cm/m⁵C/xC/C | 40/16/2/80 | 64 | Gr(p)xG/G | 1/1/87 |
| 34 | I/A | 3/20 | 65 | Ψ/U | 1/32 |
| 34 | s²U/Um/mchm⁵U/ | 1/3/1/ | 67 | Ψ/U | 2/83 |
| | ncm⁵U/cmnm⁵Um/ | 3/1/ | 67 | m²G/G | 2/64 |
| | mcm⁵s²U/mcm⁵U/ | 7/4/ | 68 | Ψ/U | 1/37 |
| | Ψ/xU/U | 1/11/5 | 72 | Ψ/U | 1/16 |
| 34 | Cm/f⁵Cm/m⁵C/xC/C | 8/1/1/2/44 | 72 | m⁵C/C | 5/132 |
| 34 | Q/RNA/manQtRNA/ | 5/4/ | | | |
| 34 | galQtRNA/Gm/G | 3/17/20 | | | |

Fig. 2B

Arg-TCA-1-1 (SEQ ID NO: 1):

GGCCGCGTGGCCTAATGGATAAGGCGTCTGACTTCAGATCAGAAGATTGCAGGTTCGAGTCCTGCCG
CGGTCG

Arg-TCA-3-1 (SEQ ID NO: 2):

GACCGCGTGGCCTAATGGATAAGGCGTCTGACTTCAGATCAGAAGATTGAGGGTTCGAGTCCCTTCG
TGGTCG

Arg-TCA-6-1 (SEQ ID NO: 3):

GGCCGTGTGGCCTAATGGATAAGGCGTCTGACTTCAGATCAAAAGATTGCAGGTTTGAGTTCTGCCA
CGGTCG

Gln-TTA-1-1 (SEQ ID NO: 16):

GGTCCCATGGTGTAATGGTTAGCACTCTGGACTTTAAATCCAGCGATCCGAGTTCAAATC
TCGGTGGGACCT

Gln-TTA-2-1 (SEQ ID NO: 17):

GGTCCCATGGTGTAATGGTTAGCACTCTGGACTTTAAATCCAGCAATCCGAGTTCGAATC
TCGGTGGGACCT

Gln-TTA-3-1 (SEQ ID NO: 18):

GGCCCCATGGTGTAATGGTTAGCACTCTGGACTTTAAATCCAGCGATCCGAGTTCAAATC
TCGGTGGGACCT

METHODS AND COMPOSITIONS FOR TREATING A PREMATURE STOP CODON-MEDIATED DISORDER

RELATED APPLICATION

This application claims priority from U.S. Provisional Application Nos. 62/736,834, filed Sep. 26, 2018, and 62/805,793, filed Feb. 14, 2019, the subject matter of which are incorporated herein by reference in their entirety.

FIELD OF THE INVENTION

This disclosure relates generally to methods and compositions for expressing a gene product encoded by a gene containing a premature stop codon and/or treating a disorder mediated by a premature stop codon.

BACKGROUND

Protein synthesis is directed by a genetic code that includes 61 three-base-pair codons encoding amino acids that are incorporated into the protein being synthesized and 3 three-base-pair codons (referred to as stop or termination codons) that terminate the synthesis of a protein. When a nucleic acid sequence encoding a protein is mutated to contain a premature stop codon rather than a codon for the next amino acid, the resulting protein is prematurely terminated, which is often nonfunctional or less functional than the untruncated or full length protein. Such mutations, termed nonsense mutations, are often associated with, or are a causative agent in numerous different genetic diseases.

A number of disorders are associated with, or are caused by nonsense mutations. These include β-thalassemia, Choroideremia (CHM), Cystic Fibrosis, Dravet Syndrome, Duchenne Muscular Dystrophy, Hurler Syndrome, KIF1A, a Lysosomal Storage Disease (e.g., Maroteaux-Lamy Syndrome, Niemann Pick Disease, and Sanfilippo Syndrome), Marfan Syndrome, Smith-Lemli-Opitz Syndrome, and Spinal Muscular Atrophy.

Dravet Syndrome is a rare and catastrophic form of intractable epilepsy that begins in infancy. Initially, patients experience prolonged seizures. In their second year, additional types of seizure begin to occur, which typically coincide with a developmental decline, possibly due to repeated cerebral hypoxia. This leads to poor development of language and motor skills. Mutations in SCN1A (encoding the voltage-gated sodium channel a subunit), SCN1B (encoding the voltage-gated sodium channel β1 subunit), SCN2A, SCN3A, SCN9A, GABRG2 (encoding the γ-aminobutyric acid receptor γ2 subunit), GABRD (encoding the γ-aminobutyric acid receptor Δ subunit) and/or PCDH19 genes have been linked to Dravet Syndrome.

For example, Dravet syndrome may be caused by a nonsense mutation in the gene resulting in a premature stop codon and a lack of or reduced amount of untruncated or functional protein. The SCN1A gene normally codes for the neuronal voltage-gated sodium channel a subunit, Na(V)1.1. In mouse models, loss-of-function mutations in SCN1A have been observed to result in a decrease in sodium currents and impaired excitability of GABAergic interneurons of the hippocampus.

Accordingly, there is a need in the art for improved compositions and methods for treating diseases mediated by premature stop codons, including Dravet syndrome.

SUMMARY

One aspect of this disclosure provides a method of expressing in a mammalian cell a functional gene product encoded by a gene containing a premature stop codon, e.g., a SCN1A gene. The method includes introducing into the cell an effective amount of an expression vector capable of expressing a tRNA that (i) comprises an anticodon that hybridizes to the premature stop codon, and (ii) is capable of being aminoacylated with an amino acid, so that the tRNA, when expressed in the cell and aminoacylated with the amino acid, hybridizes to the premature stop codon and permits the amino acid to be incorporated into the gene product at a position that would otherwise result in a truncated gene product caused by the premature stop codon.

Another aspect of this disclosure provides a method of expressing in a mammalian cell a functional gene product encoded by a gene containing a premature stop codon, e.g., a SCN1A gene. The method includes introducing into the cell an effective amount of a tRNA that (i) comprises an anticodon that hybridizes to the premature stop codon, and (ii) is capable of being aminoacylated with an amino acid, so that the tRNA, when introduced into the cell and aminoacylated with the amino acid, hybridizes to the premature stop codon and permits the amino acid to be incorporated into the gene product at a position that would otherwise result in a truncated gene product caused by the premature stop codon.

In certain embodiments of any of the foregoing methods, the gene can be an α-L-iduronidase, ARSB, β-globin, CFTR, CHM, DHCR7, dystrophin, fibrin-1 (FBN1), KIF1A, NAGLU, SCN1A, SMN1, or SMPD1 gene. In certain embodiments, the gene is a SCN1A gene.

In another aspect, this disclosure provides a method of increasing in a cell voltage-gated sodium channel activity encoded by a SCN1A gene containing a premature stop codon. The method includes introducing into the cell an effective amount of an expression vector capable of expressing a tRNA that (i) comprises an anticodon that hybridizes to the premature stop codon, and (ii) is capable of being aminoacylated with an amino acid, so that the tRNA, when expressed in the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In another aspect, this disclosure provides a method of increasing in a cell voltage-gated sodium channel activity encoded by a SCN1A gene containing a premature stop codon. The method includes introducing into the cell an effective amount of a tRNA that (i) comprises an anticodon that hybridizes to the premature stop codon, and (ii) is capable of being aminoacylated with an amino acid, so that the tRNA, when introduced into the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In certain embodiments of any of the foregoing methods, the cell contains less truncated gene product than a cell without the tRNA. In certain embodiments, the cell contains a greater amount of functional gene product than a cell without the tRNA.

In certain embodiments of any of the foregoing methods, the gene is a SCN1A gene, and the SCN1A gene product produced with the tRNA is a functional SCN1A gene product. In certain embodiments, the functional SCN1A gene product has greater activity than the truncated SCN1A gene product. In certain embodiments, the functional SCN1A gene product is the $Na_v1.1$ protein. In certain embodiments, the functional SCN1A gene product comprises a polypeptide having an amino acid sequence of SEQ ID NO: 4, SEQ ID NO: 14, or SEQ ID NO: 15. In certain embodiments, the functional SCN1A gene product comprises a polypeptide having an amino acid sequence of SEQ ID NO: 4.

In certain embodiments of any of the foregoing methods, the cell is a human cell. In certain embodiments, the cell is a central nervous system cell, e.g., a neuron. In certain embodiments, the tRNA becomes aminoacylated in the cell.

In another aspect, this disclosure provides a method of treating a premature stop codon-mediated disorder, e.g., Dravet syndrome, in a subject in need thereof, wherein the subject has a gene with a premature stop codon, e.g., a SCN1A gene. The method includes administering to the subject an effective amount of an expression vector capable of expressing a tRNA that (i) comprises an anticodon that hybridizes to the premature stop codon, and (ii) is capable of being aminoacylated with an amino acid, thereby to treat the disorder in the subject.

In another aspect, this disclosure provides a method of treating a premature stop codon-mediated disorder, e.g., Dravet syndrome, in a subject in need thereof, wherein the subject has a gene with a premature stop codon, e.g., a SCN1A gene. The method includes administering to the subject an effective amount of a tRNA that (i) comprises an anticodon that hybridizes to the premature stop codon, and (ii) is capable of being aminoacylated with an amino acid, thereby to treat the disorder in the subject.

In certain embodiments of any of the foregoing methods of treatment, the premature stop codon-mediated disorder is selected from β-thalassemia, Choroideremia (CHM), Cystic Fibrosis, Dravet Syndrome, Duchenne Muscular Dystrophy, Hurler Syndrome, KIF1A, a Lysosomal Storage Disease (e.g., Maroteaux-Lamy Syndrome, Niemann Pick Disease, and Sanfilippo Syndrome), Marfan Syndrome, Smith-Lemli-Opitz Syndrome, and Spinal Muscular Atrophy. In certain embodiments, the premature stop codon-mediated disorder is Dravet syndrome. In certain embodiments, the premature stop codon-mediated disorder is Dravet syndrome and the gene is SCN1A.

In other embodiments of any of the foregoing methods of treatment, the premature stop codon-mediated disorder is selected from epilepsy disorders, epileptic encephalopathies, Dravet Syndrome, Lennox-Gastaut Syndrome, Kleefstra Syndrome, Duchenne Muscular Dystrophy; KCNQ2 Encephalopathy, SYNGAP1 Encephalopathy, Parkinson's with GBA, CDKL5, SLC6A1, BRMUTD, Sotos Syndrome, GLUT1 Deficiency Syndrome and any other premature stop codon-mediated disorder associated with a central nervous system (CNS)-related disorder. In some embodiments, the premature stop codon-mediated disorder is selected from epilepsy disorder or epileptic encephalopathies, including Dravet Syndrome and Lennox-Gastaut Syndrome.

In still other embodiments of any of the foregoing methods of treatment, the premature stop codon-mediated disorder is selected 5q-syndrome, Adams-Oliver syndrome 1, Alagille syndrome 1, Autoimmune lymphoproliferative syndrome type 1A, Carney complex type I, CHARGE syndrome, Coffin-Siris Syndrome, Duane Syndrome, Cystic Fibrosis, Marfan Syndrome, Ehlers-Danlos Syndrome, Feingold Syndrome 1, Denys-Drash syndrome/Frasier Syndrome, DiGeorge Syndrome (TBX1-associated), Cleidocranial dysplasia, or any other non-CNS-related disorder not listed above.

In certain embodiments of any of the foregoing methods of treatment, the subject is human. In certain embodiments, the method further comprises administering DIACOMIT® (stiripentol), EPIODOLEX® (cannabidiol), a ketogenic diet, ONFI® (clobazam), TOPAMAX® (topiramate), or valproic acid to the subject.

In certain embodiments of any of the foregoing methods, the gene is a SCN1A gene, and the premature stop codon in the SCN1A gene is caused by a mutation, or a combination of mutations, selected from c.664C>T, c.1129C>T, c.1492A>T, c.1624C>T, c.1738C>T, c.1837C>T, c.2134C>T, c.2593C>T, c.3637C>T, c.3733C>T, c.3985C>T, c.4573C>T, c.5656C>T, and c.5734C>T. In certain embodiments, the premature stop is caused by a mutation selected from c.1738C>T and c.3985C>T.

In certain embodiments of any of the foregoing methods, the amino acid is selected from serine, leucine, glutamine and arginine, e.g., the amino acid is selected from glutamine and arginine, e.g., the amino acid is arginine. In certain embodiments, the anticodon hybridizes to a codon selected from UAG, UGA, and UAA, e.g., the anticodon hybridizes to a codon selected from UGA, and UAA, e.g., the anticodon hybridizes to UGA.

In certain embodiments of any of the foregoing methods, the tRNA comprises a nucleotide sequence selected from SEQ ID NO: 1, SEQ ID NO: 2, SEQ ID NO: 19, SEQ ID NO: 20, and SEQ ID NO: 21. In certain embodiments, the tRNA comprises a nucleotide sequence selected from SEQ ID NO: 1 and SEQ ID NO: 2. In certain embodiments, the tRNA comprises one or more naturally occurring nucleotide modifications, e.g., selected from 5-methyl uridine, pseudouridine, dihydrouridine, and 1-methyladeno sine.

In certain embodiments of any of the foregoing methods, the expression vector comprises a nucleotide sequence selected from SEQ ID NO: 5, SEQ ID NO: 6, SEQ ID NO: 8, SEQ ID NO: 9, SEQ ID NO: 10, SEQ ID NO: 11, SEQ ID NO: 19, SEQ ID NO: 20, and SEQ ID NO: 21. In certain embodiments, the expression vector comprises a nucleotide sequence selected from SEQ ID NO: 5, SEQ ID NO: 6, SEQ ID NO: 8, SEQ ID NO: 9, SEQ ID NO: 10, and SEQ ID NO: 11. In certain embodiments, the expression vector comprises a nucleotide sequence selected from SEQ ID NO: 19, SEQ ID NO: 20, and SEQ ID NO: 21. In certain embodiments, the expression vector is a viral vector, e.g., a DNA virus vector, e.g., an adeno-associated virus (AAV) vector.

In certain embodiments of any of the foregoing methods, the tRNA or expression vector introduced into the cell or administered to the subject is not conjugated to or associated with another moiety, e.g., a carrier particle, e.g., an aminolipid particle. In certain embodiments, the tRNA or expression vector is introduced into the cell or administered to subject in a dosage form lacking a nanoparticle. In certain embodiments, the tRNA or expression vector is introduced into the cell or administered to subject in a dosage form lacking an aminolipid delivery compound.

In another aspect, this disclosure provides a tRNA that includes the nucleotide sequence of SEQ ID NO: 1, SEQ ID NO: 2, SEQ ID NO: 16, SEQ ID NO: 17, or SEQ ID NO: 18. In certain embodiments, the tRNA comprises the nucleotide sequence of SEQ ID NO: 1 or SEQ ID NO: 2, e.g., the tRNA comprises the nucleotide sequence of SEQ ID NO: 2. In certain embodiments, the tRNA comprises the nucleotide sequence of SEQ ID NO: 16, SEQ ID NO: 17, or SEQ ID NO: 18, e.g., the tRNA comprises the nucleotide sequence of SEQ ID NO: 17 or SEQ ID NO: 18. In certain embodiments, the tRNA comprises a naturally occurring nucleotide modification, e.g., the tRNA comprises one or more nucleotide modifications selected from 5-methyl uridine, pseudouridine, dihydrouridine, and 1-methyladenosine.

In another aspect, this disclosure provides a nucleic acid comprising a nucleotide sequence encoding any of the foregoing tRNAs. In another aspect, this disclosure provides an expression vector comprising the foregoing nucleic acid. In certain embodiments, the expression vector comprises a nucleotide sequence selected from SEQ ID NO: 5, SEQ ID NO: 6, SEQ ID NO: 8, SEQ ID NO: 9, SEQ ID NO: 10, SEQ ID NO: 11, SEQ ID NO: 19, SEQ ID NO: 20, and SEQ ID NO: 21. In certain embodiments, the expression vector comprises a nucleotide sequence selected from SEQ ID NO: 5, SEQ ID NO: 6, SEQ ID NO: 8, SEQ ID NO: 9, SEQ ID NO: 10, and SEQ ID NO: 11. In certain embodiments, the expression vector comprises a nucleotide sequence selected from SEQ ID NO: 19, SEQ ID NO: 20, and SEQ ID NO: 21. In certain embodiments, the expression vector is a viral vector, e.g., a DNA virus vector, e.g., an adeno-associated virus (AAV) vector.

In another aspect, this disclosure provides a pharmaceutical composition comprising any of the foregoing tRNAs or any of the foregoing expression vectors and a pharmaceutically acceptable excipient. In certain embodiments, the tRNA or expression vector is not conjugated to, or associated with, another moiety, e.g., a carrier particle, e.g., an aminolipid particle. In certain embodiments, the composition does not include a nanoparticle and/or an aminolipid delivery compound.

These and other aspects and features of the invention are described in the following detailed description and claims.

DESCRIPTION OF THE DRAWINGS

FIG. 2B is a table showing the modification profile for tRNA sequences from the cytosol of certain eukaryotic organisms. The ratios in the table indicate the frequency of occurrence of listed nucleotide at the numbered position shown in FIG. 2A. The abbreviations for the modified residues are defined in Motorin et al. (2005) "Transfer RNA Modification," ENCYCLOPEDIA OF LIFE SCIENCES, John Wily & Sons, Inc.

DETAILED DESCRIPTION

Figure 1:
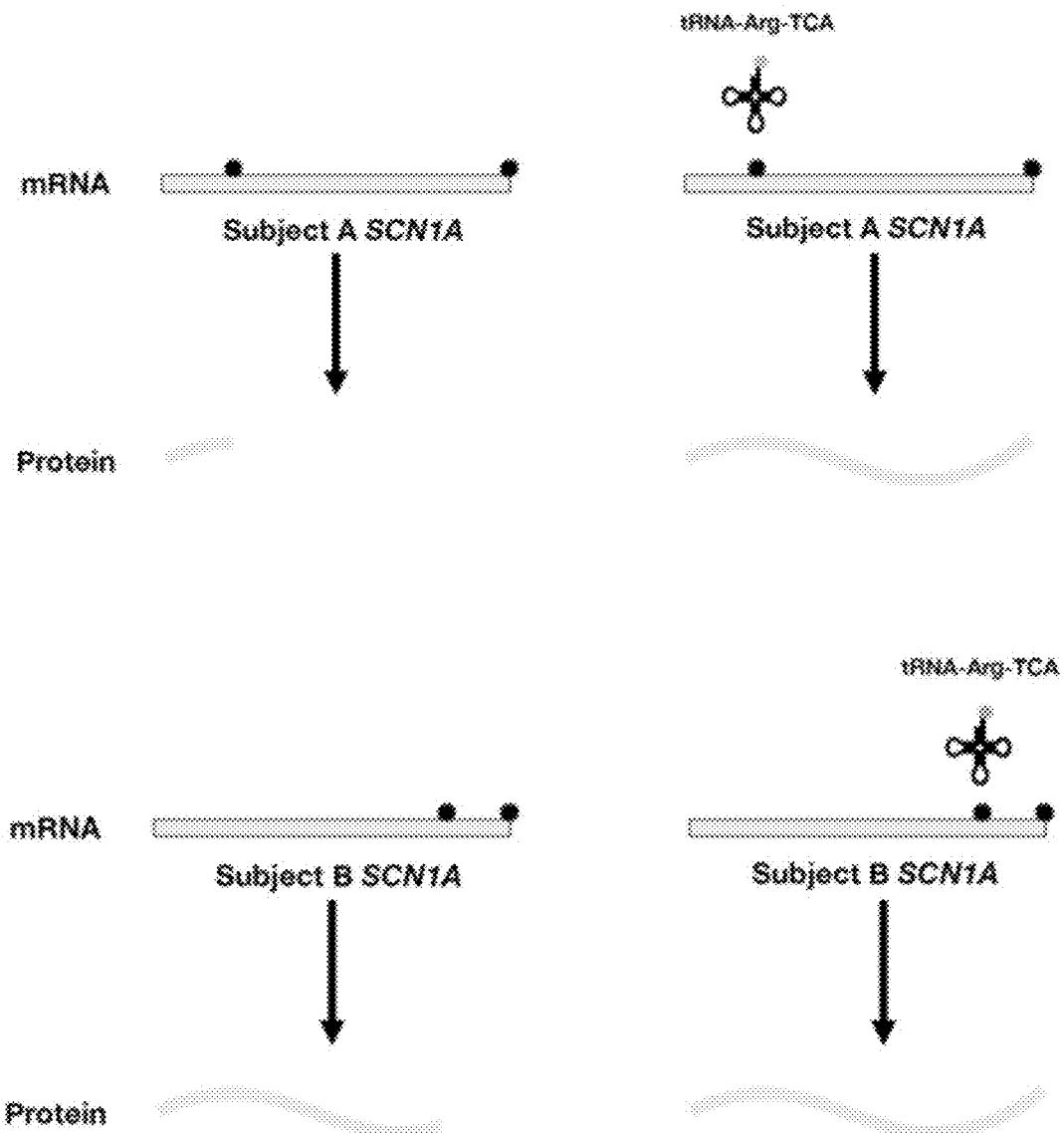
FIG. 1 is a schematic representation of SCN1A transcripts containing a premature stop codon (PSC) which leads to a truncated protein product, e.g., a protein product in a subject with Dravet syndrome. Stop codons are indicated as shaded circles, and premature stop codons are indicated as unshaded circles. Expression of a suppressor tRNA (an anticodon modified arginine tRNA) allows read-through of the PSC and facilitates expression of the full-length protein.

This disclosure relates generally to methods and compositions for expressing a gene product encoded by a gene containing a premature stop codon and/or treating a disorder mediated by a premature stop codon.

This disclosure is based, in part, upon the discovery of tRNAs (e.g., suppressor tRNAs), that permit an amino acid to be incorporated into a gene product encoded by a gene in a mammalian cell at a position that would otherwise result in a truncated gene product caused by a premature stop codon (PSC) in the gene. It was further discovered a tRNA that permits an amino acid to be incorporated into a gene product encoded by a gene at a position, which would otherwise result in a truncated gene product caused by a PSC in the gene, can be used to treat a disease mediated by a PSC in a gene in a subject.

Accordingly, in one aspect, this disclosure provides a method of expressing in a mammalian cell a functional gene product encoded by a gene containing a premature stop codon. The method includes introducing into the cell an effective amount of an expression vector capable of expressing a tRNA (e.g., as shown in TABLE 2 below) that (i) comprises an anticodon that hybridizes to the premature stop codon, and (ii) is capable of being aminoacylated with an amino acid, so that the tRNA, when expressed in the cell and aminoacylated with the amino acid, hybridizes to the premature stop codon and permits the amino acid to be incorporated into the gene product at a position that would otherwise result in a truncated gene product caused by the premature stop codon.

In another aspect, this disclosure provides a method of expressing in a mammalian cell a functional gene product encoded by a gene containing a premature stop codon. The method includes introducing into the cell an effective amount of a tRNA (e.g., as shown in TABLE 2 below) that (i) comprises an anticodon that hybridizes to the premature stop codon, and (ii) is capable of being aminoacylated with an amino acid, so that the tRNA, when introduced into the cell and aminoacylated with the amino acid, hybridizes to the premature stop codon and permits the amino acid to be incorporated into the gene product at a position that would otherwise result in a truncated gene product caused by the premature stop codon.

In certain embodiments of any of the foregoing methods, the cell contains less truncated gene product than a cell without the tRNA. For example, in certain embodiments, the cell contains about 5%, about 10%, about 20%, about 30%, about 40%, about 50%, about 60%, about 70%, about 80%, or about 90% of the truncated gene product relative to a cell without the tRNA. In certain embodiments, the cell contains from about 5% to about 80%, about 5% to about 60%, about 5% to about 40%, about 5% to about 20%, about 5% to about 10%, about 10% to about 80%, about 10% to about 60%, about 10% to about 40%, about 10% to about 20%, about 20% to about 80%, about 20% to about 60%, about 20% to about 40%, about 40% to about 80%, about 40% to about 60%, or about 60% to about 80% of the truncated gene product relative to a cell without the tRNA. In certain embodiments, there is no detectable truncated gene product in the cell. Truncated gene product amount or expression may be measured by any method known in the art, for example, Western blot or ELISA.

In certain embodiments, the cell contains a greater amount of functional gene product than a cell without the tRNA. For example, in certain embodiments, the method increases the amount of functional gene product in a cell, tissue, or subject by at least about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, or about 500% relative to a cell, tissue, or subject without the tRNA. In certain embodiments, the method increases the amount of functional gene product in a cell, tissue, or subject, by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 180%, or about 180% to about 200% relative to a cell, tissue, or subject without the tRNA. Functional gene product amount or expression may be measured by any method known in the art, for example, Western blot or ELISA.

In certain embodiments of any of the foregoing methods, the gene is selected from an α-L-iduronidase, ARSB, β-globin, CFTR, CHM, DHCR7, dystrophin, fibrin-1 (FBN1), KIF1A, NAGLU, SCN1A, SMN1, and SMPD1 gene. In certain embodiments, the gene is a SCN1A gene.

In certain embodiments, a premature stop codon in the SCN1A gene is caused by a mutation, or a combination of mutations, selected from c.58G>T, c.575G>A, c.664C>T, c.962C>G, c.1095dupT, c.1129C>T, c.1315C>T, c.1348C>T, c.1366G>T, c.1492A>T, c.1537G>T, c.1624C>T, c.1738C>T, c.1804G>T, c.1837C>T, c.2134C>T, c.2370T>A, c.2495G>A, c.2593C>T, c.2635delC, c.2904C>A, c.3295G>T, c.3311C>A, c.3452C>G, c.3637C>T, c.3656G>A, c.3733C>T, c.3783C>A, c.3829C>T, c.3985C>T, c.4359T>G, c.4547C>A, c.4573C>T, c.4721C>G, c.4954G>T, c.5641G>T, c.5656C>T, and c.5734C>T. In certain embodiments, a premature stop codon in the SCN1A gene is caused by a mutation selected from c.664C>T, c.1129C>T, c.1492A>T, c.1624C>T, c.1738C>T, c.1837C>T, c.2134C>T, c.2593C>T, c.3637C>T, c.3733C>T, c.3985C>T, c.4573C>T, c.5656C>T, and c.5734C>T. In certain embodiments, a premature stop codon in the SCN1A gene is caused by a mutation selected from c.1738C>T and c.3985C>T.

In certain embodiments, wherein the gene is a SCN1A gene, the SCN1A gene product produced with the tRNA is a functional SCN1A gene product. In certain embodiments, the functional SCN1A gene product has greater activity than the truncated SCN1A gene product, e.g., greater voltage-gated sodium channel activity. In certain embodiments, the method increases voltage-gated sodium channel activity in a cell, tissue, or subject by at least about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, or about 1000% relative to a cell, tissue, or subject without the tRNA. In certain embodiments, the method increases voltage-gated sodium channel activity in a cell, tissue, or subject by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject without the tRNA. Voltage-gated sodium channel activity may be measured by any method known in the art, for example, as described in Kalume et al. (2007) J. NEUROSCI. 27(41):11065-74, Yu et al. (2007) NAT. NEUROSCI. 9(9): 1142-9, and Han et al. (2012) NATURE 489(7416): 385-390.

In certain embodiments, the functional SCN1A gene product is the $Na_v1.1$ protein. In certain embodiments, the functional SCN1A gene product is a polypeptide that comprises, consists essentially of, or consists of the amino acid sequence of SEQ ID NO: 4, SEQ ID NO: 14, or SEQ ID NO: 15, or a polypeptide having an amino acid sequence at least 80%, 85%, 86%, 87%, 88%, 89%, 90%, 91%, 92%, 93%, 94%, 95%, 96%, 97%, 98%, or 99% identical to the amino acid sequence of SEQ ID NO: 4, SEQ ID NO: 14, or SEQ ID NO: 15.

In another aspect, this disclosure provides a method of expressing in a cell a functional SCN1A gene product encoded by a SCN1A gene containing a premature stop codon. The method includes introducing into the cell an effective amount of an expression vector capable of expressing a tRNA (e.g., as shown in TABLE 2 below) that (i) comprises an anticodon that hybridizes to the premature stop codon, and (ii) is capable of being aminoacylated with an amino acid, so that the tRNA, when expressed in the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In another aspect, this disclosure provides a method of expressing in a cell a functional SCN1A gene product encoded by a SCN1A gene containing a premature stop codon. The method includes introducing into the cell an effective amount of a tRNA (e.g., as shown in TABLE 2 below) that (i) comprises an anticodon that hybridizes to the premature stop codon, and (ii) is capable of being aminoacylated with an amino acid, so that the tRNA, when introduced into the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In another aspect, this disclosure provides a method of increasing in a cell voltage-gated sodium channel activity encoded by a SCN1A gene containing a premature stop codon. The method includes introducing into the cell an effective amount of an expression vector capable of expressing a tRNA (e.g., as shown in TABLE 2 below) that (i) comprises an anticodon that hybridizes to the premature stop codon, and (ii) is capable of being aminoacylated with an amino acid, so that the tRNA, when expressed in the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In another aspect, this disclosure provides a method of increasing in a cell voltage-gated sodium channel activity encoded by a SCN1A gene containing a premature stop codon. The method includes introducing into the cell an effective amount of a tRNA (e.g., as shown in TABLE 2 below) that (i) comprises an anticodon that hybridizes to the premature stop codon, and (ii) is capable of being aminoacylated with an amino acid, so that the tRNA, when introduced into the cell and aminoacylated with the amino acid, hybridizes to the premature stop codon and permits the amino acid to be incorporated into the SCN1A gene product at a position that would otherwise result in a truncated SCN1A gene product caused by the premature stop codon.

In certain embodiments of any of the foregoing methods, the cell is a human cell. In certain embodiments, the cell is a central nervous system cell, e.g., a neuron.

In another aspect, this disclosure provides a method of treating a premature stop codon-mediated disorder in a subject in need thereof wherein the subject has a gene with a premature stop codon. The method includes administering to the subject an effective amount of an expression vector capable of expressing a tRNA (e.g., as shown in TABLE 2 below) that (i) comprises an anticodon that hybridizes to the premature stop codon, and (ii) is capable of being aminoacylated with an amino acid, thereby to treat the disorder in the subject.

In another aspect, this disclosure provides a method of treating a premature stop codon-mediated disorder in a subject in need thereof, wherein the subject has a gene with a premature stop codon. The method includes administering to the subject an effective amount of a tRNA (e.g., as shown in TABLE 2 below) that (i) comprises an anticodon that hybridizes to the premature stop codon, and (ii) is capable of being aminoacylated with an amino acid, thereby to treat the disorder in the subject.

In certain embodiments, the premature stop codon-mediated disorder is a disorder listed in TABLE 1 below, and the gene with a premature stop codon is a gene listed in the corresponding row of TABLE 1 below.

TABLE 1

| Disorder | Gene |
| --- | --- |
| β-thalassemia | β-globin |
| Choroideremia | CHM |
| Cystic Fibrosis | CFTR |
| Dravet Syndrome | SCN1A |
| Duchenne Muscular Dystrophy | dystrophin |
| Hurler Syndrome | α-L-iduronidase |
| KIF1A | KIF1A |
| Marfan Syndrome | FBN1 |
| Maroteaux-Lamy Syndrome | ARSB |
| Niemann Pick Disease | SMPD1 |
| Sanfilippo Syndrome | NAGLU |
| Smith-Lemli-Opitz Syndrome | DHCR7 |
| Spinal Muscular Atrophy | SMN1 |

In another aspect, this disclosure provides a method of treating Dravet syndrome in a subject in need thereof wherein the subject has a SCN1A gene with a premature stop codon. The method includes administering to the subject an effective amount of an expression vector capable of expressing a tRNA (e.g., as shown in TABLE 2 below) that (i) comprises an anticodon that hybridizes to the premature stop codon, and (ii) is capable of being aminoacylated with an amino acid, thereby to treat Dravet syndrome in the subject.

In another aspect, this disclosure provides a method of treating Dravet syndrome in a subject in need thereof wherein the subject has a SCN1A gene with a premature stop codon. The method includes administering to the subject an effective amount of a tRNA (e.g., as shown in TABLE 2 below) that (i) comprises an anticodon that hybridizes to the premature stop codon, and (ii) is capable of being aminoacylated with an amino acid, thereby to treat Dravet syndrome in the subject.

In another aspect, this disclosure provides a tRNA comprising the nucleotide sequence of SEQ ID NO: 1, SEQ ID NO: 2, SEQ ID NO: 16, SEQ ID NO: 17, or SEQ ID NO: 18. In certain embodiments, the tRNA comprises the nucleotide sequence of SEQ ID NO: 1 or SEQ ID NO: 2, e.g., the tRNA comprises the nucleotide sequence of SEQ ID NO: 2. In certain embodiments, the tRNA comprises the nucleotide sequence of SEQ ID NO: 16, SEQ ID NO: 17, or SEQ ID NO: 18, e.g., the tRNA comprises the nucleotide sequence of SEQ ID NO: 17 or SEQ ID NO: 18. In another aspect, this disclosure provides a nucleic acid comprising a nucleotide sequence encoding any of the foregoing tRNAs. In another aspect, this disclosure provides an expression vector comprising the foregoing nucleic acid. In another aspect, this disclosure provides a pharmaceutical composition comprising any of the foregoing tRNAs or any of the foregoing expression vectors and a pharmaceutically acceptable excipient.

In certain embodiments of any of the foregoing methods, the tRNA or expression vector introduced into the cell or administered to the subject is not conjugated to or associated with another moiety, e.g., a carrier particle, e.g., an aminolipid particle. In certain embodiments, the tRNA or expression vector is introduced into the cell or administered to subject in a dosage form lacking a nanoparticle. In certain embodiments, the tRNA or expression vector is introduced into the cell or administered to subject in a dosage form lacking an aminolipid delivery compound, e.g., as described in U.S. Patent Publication No. 2017/0354672.

tRNAs and Suppressor tRNAs

During protein synthesis, a transfer RNA (tRNA) delivers an amino acid to a ribosome for incorporation into a growing protein (polypeptide) chain. tRNAs typically are about 70 to 100 nucleotides in length. Active tRNAs contain a 3' CCA sequence that may be transcribed into the tRNA during its synthesis or may be added later during post-transcriptional processing. During aminoacylation, the amino acid that is attached to a given tRNA molecule is covalently attached to the 2' or 3' hydroxyl group of the 3'-terminal ribose to form an aminoacyl-tRNA (aa-tRNA). It is understood that an amino acid can spontaneously migrate from the 2'-hydroxyl group to the 3'-hydroxyl group and vice versa, but it is incorporated into a growing protein chain at the ribosome from the 3'-OH position. A loop at the other end of the folded aa-tRNA molecule contains a sequence of three bases known as the anticodon. When this anticodon sequence hybridizes or base-pairs with a complementary three-base codon sequence in a ribosome-bound messenger RNA (mRNA), the aa-tRNA binds to the ribosome and its amino acid is incorporated into the polypeptide chain being synthesized by the ribosome. Because all tRNAs that base-pair with a specific codon are aminoacylated with a single specific amino acid, the translation of the genetic code is effected by tRNAs. Each of the 61 non-termination codons in an mRNA directs the binding of its cognate aa-tRNA and the addition of a single specific amino acid to the growing polypeptide chain being synthesized by the ribosome.

tRNAs are generally highly conserved and are often functional across species. Accordingly, a tRNA derived from a bacterial tRNA, a non-mammalian eukaryotic tRNA, or a mammalian (e.g., human) tRNA may be useful in the practice of the methods or compositions described herein. Nucleotide sequences encoding naturally occurring human tRNAs are known and generally available to those of skill in the art through sources such as Genbank. See also Sprinzl et al. (2005) NUCLEIC ACIDS RES. 33: D139-40; Buckland et al. (1996) GENOMICS 35(1):164-71; Schimmel et al. (Eds.) (1979) "Transfer-RNA: Structure, Properties, and Recognition," Cold Spring Harbor Laboratory; Agris (1983) "The Modified Nucleosides of Transfer RNA, II," Alan R. Liss Inc. tRNAs are generally highly conserved and are often functional across species.

Suppressor tRNAs are modified tRNAs that insert a suitable amino acid at a mutant site, e.g., a PSC, in protein encoding gene. The use of the word in suppressor is based on the fact, that under certain circumstance, the modified tRNA "suppresses" the phenotypic effect of the coding mutation. Suppressor tRNAs typically contain a mutation (modification) in either the anticodon, changing codon specificity, or at some position that alters the aminoacylation identity of the tRNA.

In certain embodiments, a tRNA (e.g., a suppressor tRNA) contains a modified anticodon region, such that the modified anticodon hybridizes with a different codon than the corresponding naturally occurring anticodon. In certain embodiments, the modified anticodon hybridizes with a stop codon, e.g., a PSC, and as a result, the tRNA incorporates an amino acid into a gene product rather than terminating protein synthesis. In certain embodiments, the modified anticodon hybridizes with a premature stop-codon and, and as a result, the tRNA incorporates an amino acid into a gene product at a position that would otherwise result in a truncated gene product caused by the premature stop codon.

In certain embodiments, a tRNA comprises an anticodon that hybridizes to a codon selected from UAG (i.e., an "amber" stop codon), UGA (i.e., an "opal" stop codon), and UAA (i.e., an "ochre" stop codon). In certain embodiments, the anticodon hybridizes to a codon selected from UGA to UAA. In certain embodiments, the anticodon hybridizes to UGA. In certain embodiments, a tRNA comprises an anticodon that hybridizes to a non-standard termination codon, e.g., a 4-nucleotide codon (See, for example, Moore et al. (2000) J. MOL. BIOL. 298:195, and Hohsaka et al. (1999) J. AM. CHEM. SOC. 121:12194).

In certain embodiments, the tRNA is aminoacylated or is capable of being aminoacylated with any natural amino acid. For example, a tRNA may be capable of being aminoacylated with alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In certain embodiments, the tRNA is capable of being aminoacylated with serine, leucine, glutamine, or arginine. In certain embodiments, the tRNA is capable of being aminoacylated with glutamine or arginine. In certain embodiments, the tRNA is capable of being aminoacylated with arginine.

In certain embodiments, the tRNA (i) comprises an anticodon that hybridizes to a codon as indicated in TABLE 2, and (ii) is aminoacylated or is capable of being aminoacylated with an amino acid as indicated in TABLE 2.

TABLE 2

| | | |
|---|---|---|
| codon: UAG | codon: UGA | codon: UAA |
| amino acid: alanine | amino acid: alanine | amino acid: alanine |
| codon: UAG | codon: UGA | codon: UAA |
| amino acid: arginine | amino acid: arginine | amino acid: arginine |
| codon: UAG | codon: UGA | codon: UAA |
| amino acid: asparagine | amino acid: asparagine | amino acid: asparagine |
| codon: UAG | codon: UGA | codon: UAA |
| amino acid: aspartic acid | amino acid: aspartic acid | amino acid: aspartic acid |
| codon: UAG | codon: UGA | codon: UAA |
| amino acid: cysteine | amino acid: cysteine | amino acid: cysteine |
| codon: UAG | codon: UGA | codon: UAA |
| amino acid: glutamine | amino acid: glutamine | amino acid: glutamine |
| codon: UAG | codon: UGA | codon: UAA |
| amino acid: glutamic acid | amino acid: glutamic acid | amino acid: glutamic acid |
| codon: UAG | codon: UGA | codon: UAA |
| amino acid: glycine | amino acid: glycine | amino acid: glycine |
| codon: UAG | codon: UGA | codon: UAA |
| amino acid: histidine | amino acid: histidine | amino acid: histidine |
| codon: UAG | codon: UGA | codon: UAA |
| amino acid: isoleucine | amino acid: isoleucine | amino acid: isoleucine |
| codon: UAG | codon: UGA | codon: UAA |
| amino acid: leucine | amino acid: leucine | amino acid: leucine |

TABLE 2-continued

| codon: UAG | codon: UGA | codon: UAA |
|---|---|---|
| amino acid: lysine | amino acid: lysine | amino acid: lysine |
| codon: UAG | codon: UGA | codon: UAA |
| amino acid: methionine | amino acid: methionine | amino acid: methionine |
| codon: UAG | codon: UGA | codon: UAA |
| amino acid: phenylalanine | amino acid: phenylalanine | amino acid: phenylalanine |
| codon: UAG | codon: UGA | codon: UAA |
| amino acid: proline | amino acid: proline | amino acid: proline |
| codon: UAG | codon: UGA | codon: UAA |
| amino acid: serine | amino acid: serine | amino acid: serine |
| codon: UAG | codon: UGA | codon: UAA |
| amino acid: threonine | amino acid: threonine | amino acid: threonine |
| codon: UAG | codon: UGA | codon: UAA |
| amino acid: tryptophan | amino acid: tryptophan | amino acid: tryptophan |
| codon: UAG | codon: UGA | codon: UAA |
| amino acid: tyrosine | amino acid: tyrosine | amino acid: tyrosine |
| codon: UAG | codon: UGA | codon: UAA |
| amino acid: valine | amino acid: valine | amino acid: valine |

In certain embodiments, a tRNA comprises, consists essentially of, or consists of the nucleotide sequence of SEQ ID NO: 1, SEQ ID NO: 2, SEQ ID NO: 16, SEQ ID NO: 17, or SEQ ID NO: 18, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, SEQ ID NO: 2, SEQ ID NO: 16, SEQ ID NO: 17, or SEQ ID NO: 18.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul (1993) J. MOL. EVOL. 36, 290-300; Altschul et al., (1997) NUCLEIC ACIDS RES. 25:3389-3402) are tailored for sequence similarity searching. For a discussion of basic issues in searching sequence databases see Altschul et al. (1994) NATURE GENETICS 6:119-129. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: —G, Cost to open gap [Integer]: default=5 for nucleotides/11 for proteins; —E, Cost to extend gap [Integer]: default=2 for nucleotides/1 for proteins; —q, Penalty for nucleotide mismatch [Integer]: default=−3; —r, reward for nucleotide match [Integer]: default=1; —e, expect value [Real]: default=10; —W, wordsize [Integer]: default=11 for nucleotides/28 for megablast/3 for proteins; —y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

It is contemplated that a tRNA may comprise on or more modifications. Exemplary modified tRNAs include: acylated tRNA; alkylated tRNA; a tRNA containing one or more bases other than adenine, cytosine, guanine, or uracil; a tRNA covalently modified by the attachment of a specific ligand or antigenic, fluorescent, affinity, reactive, spectral, or other probe moiety; a tRNA containing one or more ribose moieties that are methylated or otherwise modified; aa-tRNAs that are aminoacylated with an amino acid other than the 20 natural amino acids, including non-natural amino acids that function as a carrier for reagents, specific ligands, or as an antigentic, fluorescent, reactive, affinity, spectral, or other probe; or any combination of these compositions. Exemplary modified tRNA molecules are described in Soll et al. (1995) "tRNA: Structure, Biosynthesis, and Function," ASM Press; El Yacoubi et al. (2012) ANNU. REV. GENET. 46:69-95; Grosjean et al. (1998) "Modification and Editing of RNA." ASM Press; Hendrickson et al. (2004) ANNU. REV. BIOCHEM. 73:147-176, 2004; Ibba et al. (2000) ANNU. REV. BIOCHEM. 69:617-650; Johnson et al. (1995) COLD SPRING HARBOR SYMP. QUANT. BIOL. 60:71-82; Johnson et al. (1982) J. MOL. BIOL. 156:113-140; Crowley et al. (1994) CELL 78:61-71; Beier et al. (2001) NUCLEIC ACIDS RES. 29:4767-4782; Tones et al. (2014) TRENDS MOL. MED. 20:306-314; and Bjork et al. (1987) ANNU. REV. BIOCHEM. 56:263-287.

Figure 2A:
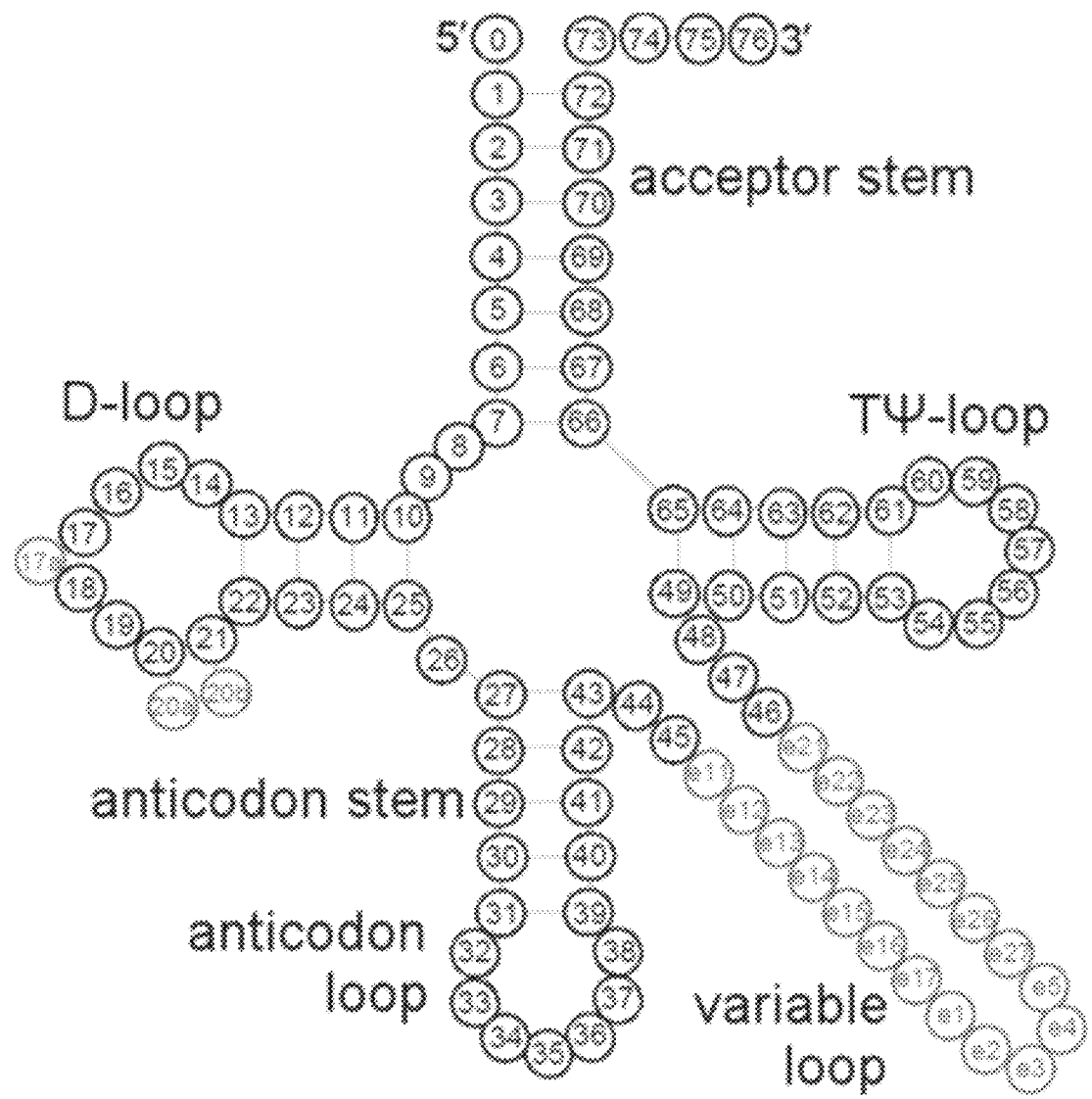
FIG. 2A is a consensus tRNA secondary structure. The numbering of the residues is based on the tRNA numbering system described in Steinberg et al. (1993) NUCLEIC ACIDS RES. 21:3011-15.

In certain embodiments, a tRNA comprises a naturally occurring nucleotide modification. Naturally occurring tRNAs contain a wide variety of post-transcriptionally modified nucleotides, which are described, for example, in Machnicka et al. (2014) RNA BIOLOGY 11(12): 1619-1629, and include one or more of the residues as shown in FIG. 2B. In certain embodiments, the tRNA comprises one or more of the residues selected from the group consisting of: 2'-O-methylguanosine or G at position 0; pseudouridine or U at position 1; 2'-O-methyladenosine, A, 2'-O-methyluridine, U, 2'-O-methylcytidine, C, 2'-O-methylguanosine, or G at position 4; N2-methylguanosine or G at position 6; N2-methylguanosine or G at position 7; 1-methyladenosine, A, 1-methylguanosine, G, or a modified G at position 9; N2-methylguanosine or G at position 10; N4-acetylcytidine or C at position 12; pseudouridine, U, 2'-O-methylcytidine, or C at position 13; 1-methyladenosine, A, or a modified A at position 14; dihydrouridine (D) or U at position 16; D or U at position 17; 2'-O-methylguanosine or G at position 18; 3-(3-amino-3-carboxypropyl)uridine, D, or U at position 20; 3-(3-amino-3-carboxypropyl)uridine, D, pseudouridine, U, or a modified U at position 20a; D, pseudouridine, or U at position 20b; pseudouridine or U at position 25; pseudouridine, U, N2,N2-dimethylguanosine, N2-methylguanosine, G, or a modified G at position 26; pseudouridine, U, N2,N2-dimethylguanosine, or G at position 27; pseudouridine or U at position 28; pseudouridine or U at position 30; pseudouridine or U at position 31; 2'-O-methylpseudouridine, 2'-O-methyluridine, pseudouridine, U, 2'-O-methylcytidine, 3-methylcytidine, C, or a modified C at position 32; inosine, A, 2-thiouridine, 2'-O-methyluridine, 5-(carboxyhydroxymethyl)uridine methyl ester, 5-carbamoylmethyluridine, 5-carboxymethylaminomethyl-2'-O-methyluridine, 5-methoxycarbonylmethyl-2-thiouridine, 5-methoxycarbonylmethyluridine, pseudouridine, U, a modified U, 2'-O-methylcytidine, 5-formyl-2'-O-methylcytidine, 5-methylcytidine, C, a modified C, queuosine, mannosyl-queuosine, galactosyl-queuosine, 2'-O-methylguanosine, or G at position 34; pseudouridine or U at position 35; pseudouridine, U, or a modified U at position 36; 1-methylinosine, 2-methylthio-N6-threonylcarbamoyladenosine, N6-isopentenyladenosine, N6-methyl-N6-threonylcarbamoyladenosine, N6-threonylcarbamoyladenosine, A, a modified A, 1-methylguanosine, peroxywybutosine, wybutosine, G, or a modified G at position 37; pseudouridine, U, 5-methylcytidine, C, or a modified C at position 38; 1-methylpseudouridine, 2'-O-methylpseudouridine, 2'-O-methyluridine, pseudouridine, U, 2'-O-methylguanosine, or G at position 39; pseudouridine, U, 5-methylcytidine, or C at position 40; 2'-O-methyluridine, U, or a modified U at position 44; pseudouridine or U at position e11; pseudouridine or U at position e12; pseudouridine or U at position e14; 3-methylcytidine or C at position e2; 7-methylguanosine or G at position 46; D, U, or a modified U at position 47; D, U, 5-methylcytidine, C, or a modified C at position 48; A, a modified A, 5-methylcytidine, C, or a modified C at position 49; pseudouridine, U, 5-methylcytidine, or C at position 50; 5,2'-O-dimethyluridine, 5-methyluridine, pseudouridine, or U at position 54; pseudouridine or U at position 55; 1-methyladenosine, A, or a modified A at position 58; 2'-O-ribosyladenosine (phosphate), A, 2'-O-ribosylguanosine (phosphate), G, or a modified G at position 64; pseudouridine or U at position 65; pseudouridine, U, N2-methylguanosine, or G at position 67; pseudouridine or U at position 68; and, pseudouridine, U, 5-methylcytidine, or C at position 72. A, C, G, and U, refer to unmodified adenine, cytosine, guanine, and uracil, respectively. The numbering of the residues is based on the tRNA numbering system described in Steinberg et al., (1993) NUCLEIC ACIDS RES. 21:3011-15.

In certain embodiments, the tRNA comprises one or more nucleotide modifications selected from 5-methyl uridine, pseudouridine, dihydrouridine, and 1-methyladenosine.

Methods Of Making tRNAs

It is contemplated the tRNA molecules (e.g., suppressor tRNAs) useful in the methods and compositions described herein can be produced by methods known in the art, including extracellular production by synthetic chemical methods, intracellular production by recombinant DNA methods, or purification from natural sources.

For example, DNA molecules encoding tRNAs can be synthesized chemically or by recombinant DNA methodologies. For example, the sequences of the tRNAs can be synthesized or cloned from libraries by conventional hybridization techniques or polymerase chain reaction (PCR) techniques, using the appropriate synthetic nucleic acid primers. The resulting DNA molecules encoding the tRNAs can be ligated to other appropriate nucleotide sequences, including, for example, expression control sequences to produce conventional gene expression constructs (i.e., expression vectors) encoding the tRNAs. Production of defined gene constructs is within routine skill in the art. Nucleic acids encoding desired tRNAs can be incorporated (ligated) into expression vectors, such as the expression vectors described in the following section, which can be introduced into host cells through conventional transfection or transformation techniques. Examples of host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the tRNAs. Specific expression and purification conditions will vary depending upon the expression system employed.

Alternatively, tRNAs can be chemically synthesized or purified from natural sources by methods known in art. When a tRNA is aminoacylated prior to introduction into the cell or administration to the subject, the tRNA may be aminoacylated with a desired amino acid by any method known in the art, including chemical or enzymatic aminoacylation.

Expression Vectors

The tRNAs of interest may be expressed in a cell of interest by incorporating a gene encoding a tRNA of interest into an appropriate expression vector. As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide of interest.

In certain embodiments, the expression vector is a viral vector. The term "virus" is used herein to refer to an obligate intracellular parasite having no protein-synthesizing or energy-generating mechanism. Exemplary viral vectors include retroviral vectors (e.g., lentiviral vectors), adenoviral vectors, adeno-associated viral vectors, herpesviruses vectors, epstein-barr virus (EBV) vectors, polyomavirus vectors (e.g., simian vacuolating virus 40 (SV40) vectors), poxvirus vectors, and pseudotype virus vectors.

The virus may be a RNA virus (having a genome that is composed of RNA) or a DNA virus (having a genome composed of DNA). In certain embodiments, the viral vector is a DNA virus vector. Examples of DNA viruses include parvoviruses (e.g., adeno-associated viruses), adenoviruses, asfarviruses, herpesviruses (e.g., herpes simplex virus 1 and 2 (HSV-1 and HSV-2), epstein-barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). In certain embodiments, the viral vector is a RNA virus vector. Examples of RNA viruses include bunyaviruses (e.g., hantavirus), coronaviruses, flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses.

In certain embodiments, the expression vector comprises a regulatory sequence or promoter operably linked to the nucleotide sequence encoding the tRNA. The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

tRNA genes can have strong promoters that are active in a variety of cell types. The promoters for eukaryotic tRNA genes typically are present within the structural sequences encoding the tRNA molecule itself. Although there are elements, which regulate transcriptional activity within the 5' upstream region, the length of an active transcriptional unit may be considerably less than 500 base pairs.

Additional examples of promoters, which may be employed, include, but are not limited to, the retroviral LTR, the SV40 promoter, the human cytomegalovirus (CMV) promoter, the U6 promoter, or any other promoter (e.g., cellular promoters such as eukaryotic cellular promoters including, but not limited to, the histone, pol III, and β-actin promoters). Other viral promoters, which may be employed, include, but are not limited to, adenovirus promoters, TK promoters, and B19 parvovirus promoters. The selection of a promoter will be apparent to those skilled in the art from the teachings contained herein.

In certain embodiments, an expression vector includes a tRNA coding sequence comprising, consisting essentially of, or consisting of the nucleotide sequence of SEQ ID NO: 1, SEQ ID NO: 2, SEQ ID NO: 16, SEQ ID NO: 17, or SEQ ID NO: 18, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, SEQ ID NO: 2, SEQ ID NO: 16, SEQ ID NO: 17, or SEQ ID NO: 18.

In certain embodiments, in addition to a tRNA coding sequence, the expression vector comprises a nucleotide sequence corresponding to the genomic DNA sequence flanking a corresponding wild-type tRNA gene. For example, in certain embodiments, an expression vector comprises, consists essentially of, or consists of the nucleotide sequence of SEQ ID NO: 5, SEQ ID NO: 6, SEQ ID NO: 8, SEQ ID NO: 9, SEQ ID NO: 10, SEQ ID NO: 11, SEQ ID NO: 19, SEQ ID NO: 20, or SEQ ID NO: 21, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 5, SEQ ID NO: 6, SEQ ID NO: 8, SEQ ID NO: 9, SEQ ID NO: 10, SEQ ID NO: 11, SEQ ID NO: 19, SEQ ID NO: 20, or SEQ ID NO: 21.

Adeno-Associated Virus (AAV) Vectors

In certain embodiments, an expression vector is an adeno-associated virus (AAV) vector. AAV is a small, nonenveloped icosahedral virus of the genus Dependoparvovirus and family Parvovirus. AAV has a single-stranded linear DNA genome of approximately 4.7 kb. AAV is capable of infecting both dividing and quiescent cells of several tissue types, with different AAV serotypes exhibiting different tissue tropism.

AAV includes numerous serologically distinguishable types including serotypes AAV-1 to AAV-12, as well as more than 100 serotypes from nonhuman primates (See, e.g., Srivastava (2008) J. CELL BIOCHEM., 105(1): 17-24, and Gao et al. (2004) J. VIROL., 78(12), 6381-6388). The serotype of the AAV vector used in the methods and compositions described herein can be selected by a skilled person in the art based on the efficiency of delivery, tissue tropism, and immunogenicity. For example, AAV-1, AAV-2, AAV-4, AAV-5, AAV-8, and AAV-9 can be used for delivery to the central nervous system; AAV-1, AAV-8, and AAV-9 can be used for delivery to the heart; AAV-2 can be used for delivery to the kidney; AAV-7, AAV-8, and AAV-9 can be used for delivery to the liver; AAV-4, AAV-5, AAV-6, AAV-9 can be used for delivery to the lung, AAV-8 can be used for delivery to the pancreas, AAV-2, AAV-5, and AAV-8 can be used for delivery to the photoreceptor cells; AAV-1, AAV-2, AAV-4, AAV-5, and AAV-8 can be used for delivery to the retinal pigment epithelium; AAV-1, AAV-6, AAV-7, AAV-8, and AAV-9 can be used for delivery to the skeletal muscle. In certain embodiments, the AAV capsid protein comprises a sequence as disclosed in U.S. Pat. No. 7,198,951, such as, but not limited to, AAV-9 (SEQ ID NOs: 1-3 of U.S. Pat. No. 7,198,951), AAV-2 (SEQ ID NO: 4 of U.S. Pat. No. 7,198, 951), AAV-1 (SEQ ID NO: 5 of U.S. Pat. No. 7,198,951), AAV-3 (SEQ ID NO: 6 of U.S. Pat. No. 7,198,951), and AAV-8 (SEQ ID NO: 7 of U.S. Pat. No. 7,198,951). AAV serotypes identified from rhesus monkeys, e.g., rh.8, rh.10, rh.39, rh.43, and rh.74, are also contemplated in the compositions and methods described herein. Besides the natural AAV serotypes, modified AAV capsids have been developed for improving efficiency of delivery, tissue tropism, and immunogenicity. Exemplary natural and modified AAV capsids are disclosed in U.S. Pat. Nos. 7,906,111, 9,493,788, and 7,198,951, and PCT Publication No. WO2017189964A2.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous gene of interest. Accordingly, in certain embodiments, the AAV vector comprises a genome comprising an expression cassette for an exogenous gene flanked by a 5' ITR and a 3' ITR. The ITRs may be derived from the same serotype as the capsid or a derivative thereof. Alternatively, the ITRs may be of a different serotype from the capsid, thereby generating a pseudotyped AAV. In certain embodiments, the ITRs are derived from AAV-2. In certain embodiments, the ITRs are derived from AAV-5. At least one of the ITRs may be modified to mutate or delete the terminal resolution site, thereby allowing production of a self-complementary AAV vector.

The rep and cap proteins can be provided in trans, for example, on a plasmid, to produce an AAV vector. A host cell line permissive of AAV replication must express the rep and cap genes, the ITR-flanked expression cassette, and helper functions provided by a helper virus, for example adenoviral genes Ela, E1b55K, E2a, E4orf6, and VA (Weitzman et al., Adeno-associated virus biology. Adeno-Associated Virus: Methods and Protocols, pp. 1-23, 2011). Methods for generating and purifying AAV vectors have been described in detail (See e.g., Mueller et al., (2012) CURRENT PROTOCOLS IN MICROBIOLOGY, 14D.1.1-14D.1.21, Production and Discovery of Novel Recombinant Adeno-Associated Viral Vectors). Numerous cell types can be used for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, and 8,163,543, U.S. Patent Publication No. 20020081721, and PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the methods and compositions described herein. Similarly, it is contemplated that any adenoviral type may be used, and a person of skill in the art will be able to identify AAV and adenoviral types that can be used for the production of their desired recombinant AAV vector (rAAV). AAV particles may be purified, for example, by affinity chromatography, iodixonal gradient, or CsCl gradient.

AAV vectors may have single-stranded genomes that are 4.7 kb in size, or are larger or smaller than 4.7 kb, including oversized genomes that are as large as 5.2 kb, or as small as 3.0 kb. Thus, where the exogenous gene of interest to be expressed from the AAV vector is small, the AAV genome may comprise a stuffer sequence. Further, vector genomes may be substantially self-complementary thereby allowing for rapid expression in the cell. In certain embodiments, the genome of a self-complementary AAV vector comprises from 5' to 3': a 5' ITR; a first nucleic acid sequence comprising a promoter and/or enhancer operably linked to a coding sequence of a gene of interest; a modified ITR that does not have a functional terminal resolution site; a second nucleic acid sequence complementary or substantially complementary to the first nucleic acid sequence; and a 3' ITR. AAV vectors containing genomes of all types are can be used in the methods described herein.

Non-limiting examples of AAV vectors include pAAV-MCS (Agilent Technologies), pAAVK-EF1α-MCS (System Bio Catalog #AAV502A-1), pAAVK-EF1α-MCS1-CMV-MCS2 (System Bio Catalog #AAV503A-1), pAAV-Zs-Greenl (Clontech Catalog #6231), pAAV-MCS2 (Addgene Plasmid #46954), AAV-Stuffer (Addgene Plasmid #106248), pAAVscCBPIGpluc (Addgene Plasmid #35645), AAVS1_Puro_PGK1_3×FLAG_Twin_Strep (Addgene Plasmid #68375), pAAV-RAM-d2TTA::TRE-MCS-WPRE-pA (Addgene Plasmid #63931), pAAV-UbC (Addgene Plasmid #62806), pAAVS1-P-MCS (Addgene Plasmid #80488), pAAV-Gateway (Addgene Plasmid #32671), pAAV-Puro_siKD (Addgene Plasmid #86695), pAAVS1-Nst-MCS (Addgene Plasmid #80487), pAAVS1-Nst-CAG-DEST (Addgene Plasmid #80489), pAAVS1-P-CAG-DEST (Addgene Plasmid #80490), pAAVf-EnhCB-lacZnls (Addgene Plasmid #35642), and pAAVS1-shRNA (Addgene Plasmid #82697). These vectors can be modified for therapeutic use. For example, an exogenous gene of interest can be inserted in a multiple cloning site, and a selection marker (e.g., puro or a gene encoding a fluorescent protein) can be deleted or replaced with another (same or different) exogenous gene of interest. Further examples of AAV vectors are disclosed in U.S. Pat. Nos. 5,871,982, 6,270,996, 7,238,526, 6,943,019, 6,953,690, 9,150,882, and 8,298,818, U.S. Patent Publication No. 2009/0087413, and PCT Publication Nos. WO2017075335A1, WO2017075338A2, and WO2017201258A1.

In certain embodiments, the expression vector is an AAV vector capable of targeting the nervous system, e.g., the central nervous system, in a subject, e.g., a human subject. Exemplary AAV vectors that can target the nervous system include the AAV9 variants AAV-PHP.B (See, e.g., Deverman et al. (2016) NAT. BIOTECHNOL. 34(2):204-209), AAV-AS (See, e.g., Choudhury et al. (2016) MOL. THER. 24:726-35), and AAV-PHP.eB (See, e.g., Chan et al. (2017) NAT. NEUROSCI. 20:1172-79). Additional exemplary AAV-based strategies for targeting the nervous system are described in Bedrook et al. (2018) ANNU REV NEUROSCI. 41:323-348.

Lentivirus Vectors

In certain embodiments, the viral vector can be a retroviral vector. Examples of retroviral vectors include moloney murine leukemia virus vectors, spleen necrosis virus vectors, and vectors derived from retroviruses, such as rous sarcoma virus, harvey sarcoma virus, avian leukosis virus, human immunodeficiency virus, myeloproliferative sarcoma virus, and mammary tumor virus. Retroviral vectors are useful as agents to mediate retroviral-mediated gene transfer into eukaryotic cells.

In certain embodiments, the retroviral vector is a lentiviral vector. Exemplary lentiviral vectors include vectors derived from human immunodeficiency virus-1 (HIV-1), human immunodeficiency virus-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), and caprine arthritis encephalitis virus (CAEV).

Retroviral vectors typically are constructed such that the majority of sequences coding for the structural genes of the virus are deleted and replaced by the gene(s) of interest. Often, the structural genes (i.e., gag, pol, and env), are removed from the retroviral backbone using genetic engineering techniques known in the art. Accordingly, a minimum retroviral vector comprises from 5' to 3': a 5' long terminal repeat (LTR), a packaging signal, an optional exogenous promoter and/or enhancer, an exogenous gene of interest, and a 3' LTR. If no exogenous promoter is provided, gene expression is driven by the 5' LTR, which is a weak promoter and requires the presence of Tat to activate expression. The structural genes can be provided in separate vectors for manufacture of the lentivirus, rendering the produced virions replication-defective. Specifically, with respect to lentivirus, the packaging system may comprise a single packaging vector encoding the Gag, Pol, Rev, and Tat genes, and a third, separate vector encoding the envelope protein Env (usually VSV-G due to its wide infectivity). To improve the safety of the packaging system, the packaging vector can be split, expressing Rev from one vector, Gag and Pol from another vector. Tat can also be eliminated from the packaging system by using a retroviral vector comprising a chimeric 5' LTR, wherein the U3 region of the 5' LTR is replaced with a heterologous regulatory element.

The genes can be incorporated into the proviral backbone in several general ways. The most straightforward constructions are ones in which the structural genes of the retrovirus are replaced by a single gene that is transcribed under the control of the viral regulatory sequences within the LTR. Retroviral vectors have also been constructed that can introduce more than one gene into target cells. Usually, in such vectors one gene is under the regulatory control of the viral LTR, while the second gene is expressed either off a spliced message or is under the regulation of its own, internal promoter.

Accordingly, the new gene(s) are flanked by 5' and 3' LTRs, which serve to promote transcription and polyadenylation of the virion RNAs, respectively. The term "long terminal repeat" or "LTR" refers to domains of base pairs located at the ends of retroviral DNAs which, in their natural sequence context, are direct repeats and contain U3, R and U5 regions. LTRs generally provide functions fundamental to the expression of retroviral genes (e.g.,promotion, initiation and polyadenylation of gene transcripts) and to viral replication. The LTR contains numerous regulatory signals including transcriptional control elements, polyadenylation signals, and sequences needed for replication and integration of the viral genome. The U3 region contains the enhancer and promoter elements. The U5 region is the sequence between the primer binding site and the R region and contains the polyadenylation sequence. The R (repeat) region is flanked by the U3 and U5 regions. In certain embodiments, the R region comprises a trans-activation response (TAR) genetic element, which interacts with the trans-activator (tat) genetic element to enhance viral replication. This element is not required in embodiments wherein the U3 region of the 5' LTR is replaced by a heterologous promoter.

In certain embodiments, the retroviral vector comprises a modified 5' LTR and/or 3' LTR. Modifications of the 3' LTR are often made to improve the safety of lentiviral or retroviral systems by rendering viruses replication-defective. In specific embodiments, the retroviral vector is a self-inactivating (SIN) vector. As used herein, a SIN retroviral vector refers to a replication-defective retroviral vector in which the 3' LTR U3 region has been modified (e.g., by deletion or substitution) to prevent viral transcription beyond the first round of viral replication. This is because the 3' LTR U3 region is used as a template for the 5' LTR U3 region during viral replication and, thus, the viral transcript cannot be made without the U3 enhancer-promoter. In a further embodiment, the 3' LTR is modified such that the U5 region is replaced, for example, with an ideal polyadenylation sequence. It should be noted that modifications to the LTRs such as modifications to the 3' LTR, the 5' LTR, or both 3' and 5' LTRs, are also included in the methods and compositions described herein.

In certain embodiments, the U3 region of the 5' LTR is replaced with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus, because there is no complete U3 sequence in the virus production system.

Adjacent the 5' LTR are sequences necessary for reverse transcription of the genome (the tRNA primer binding site) and for efficient packaging of viral RNA into particles (the Psi site). As used herein, the term "packaging signal" or "packaging sequence" refers to sequences located within the retroviral genome which are required for encapsidation of retroviral RNA strands during viral particle formation (see e.g., Clever et al., 1995 J. VIROLOGY, 69(4):2101-09). The packaging signal may be a minimal packaging signal (also referred to as the psi [Ψ] sequence) needed for encapsidation of the viral genome.

In certain embodiments, the retroviral vector (e.g., lentiviral vector) further comprises a FLAP. As used herein, the term "FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou et al. (2000) CELL, 101:173. During reverse transcription, central initiation of the plus-strand DNA at the cPPT and central termination at the CTS lead to the formation of a three-stranded DNA structure: a central DNA flap. While not wishing to be bound by any theory, the DNA flap may act as a cis-active determinant of lentiviral genome nuclear import and/or may increase the titer of the virus. In particular embodiments, the retroviral vector backbones comprise one or more FLAP elements upstream or downstream of the heterologous genes of interest in the vectors. For example, in particular embodiments, a transfer plasmid includes a FLAP element. In one embodiment, a vector described herein comprises a FLAP element isolated from HIV-1.

In certain embodiments, the retroviral vector (e.g., lentiviral vector) further comprises an export element. In one embodiment, retroviral vectors comprise one or more export elements. The term "export element" refers to a cis-acting post-transcriptional regulatory element, which regulates the transport of an RNA transcript from the nucleus to the cytoplasm of a cell. Examples of RNA export elements include, but are not limited to, the human immunodeficiency virus (HIV) RRE (see e.g., Cullen et al., (1991) J. VIROL. 65: 1053; and Cullen et al., (1991) CELL 58: 423) and the hepatitis B virus post-transcriptional regulatory element (HPRE). Generally, the RNA export element is placed within the 3' UTR of a gene, and can be inserted as one or multiple copies.

In certain embodiments, the retroviral vector (e.g., lentiviral vector) further comprises a posttranscriptional regulatory element. A variety of posttranscriptional regulatory elements can increase expression of a heterologous nucleic acid, e.g., woodchuck hepatitis virus posttranscriptional regulatory element (WPRE; see Zufferey et al., (1999) J. VIROL., 73:2886); the posttranscriptional regulatory element present in hepatitis B virus (HPRE) (Huang et al., MOL. CELL. BIOL., 5:3864); and the like (Liu et al., (1995), GENES DEV., 9:1766). The posttranscriptional regulatory element is generally positioned at the 3' end the heterologous nucleic acid sequence. This configuration results in synthesis of an mRNA transcript whose 5' portion comprises the heterologous nucleic acid coding sequences and whose 3' portion comprises the posttranscriptional regulatory element sequence. In certain embodiments, vectors described herein lack or do not comprise a posttranscriptional regulatory element such as a WPRE or HPRE, because in some instances these elements increase the risk of cellular transformation and/or do not substantially or significantly increase the amount of mRNA transcript or increase mRNA stability. Therefore, in certain embodiments, vectors described herein lack or do not comprise a WPRE or HPRE as an added safety measure.

Elements directing the efficient termination and polyadenylation of the heterologous nucleic acid transcripts increase heterologous gene expression. Transcription termination signals are generally found downstream of the polyadenylation signal. Accordingly, in certain embodiments, the retroviral vector (e.g., lentiviral vector) further comprises a polyadenylation signal. The term "polyadenylation signal" or "polyadenylation sequence" as used herein denotes a DNA sequence which directs both the termination and polyadenylation of the nascent RNA transcript by RNA polymerase H. Efficient polyadenylation of the recombinant transcript is desirable as transcripts lacking a polyadenylation signal are unstable and are rapidly degraded. Illustrative examples of polyadenylation signals that can be used in a vector described herein, includes an ideal polyadenylation sequence (e.g., AATAAA, ATTAAA AGTAAA), a bovine growth hormone polyadenylation sequence (BGHpA), a rabbit β-globin polyadenylation sequence (rβgpA), or another suitable heterologous or endogenous polyadenylation sequence known in the art.

In certain embodiments, a retroviral vector further comprises an insulator element. Insulator elements may contribute to protecting retrovirus-expressed sequences, e.g., therapeutic genes, from integration site effects, which may be mediated by cis-acting elements present in genomic DNA and lead to deregulated expression of transferred sequences (i.e., position effect; see, e.g., Burgess-Beusse et al., (2002) PROC. NATL. ACAD. SCI., USA, 99:16433; and Zhan et al., 2001, HUM. GENET., 109:471). In certain embodiments, the retroviral vector comprises an insulator element in one or both LTRs or elsewhere in the region of the vector that integrates into the cellular genome. Examples of insulators for use in the methods and compositions described herein include, but are not limited to, the chicken β-globin insulator (see Chung et al., (1993). CELL 74:505; Chung et al., (1997) PROC. NATL. ACAD. SCI., USA 94:575; and Bell et al., 1999. CELL 98:387). Examples of insulator elements include, but are not limited to, an insulator from a 3-globin locus, such as chicken HS4.

Non-limiting examples of lentiviral vectors include pLVX-EFlalpha-AcGFP1-C1 (Clontech Catalog #631984), pLVX-EFlalpha-IRES-mCherry (Clontech Catalog #631987), pLVX-Puro (Clontech Catalog #632159), pLVX-IRES-Puro (Clontech Catalog #632186), pLenti6/V5-DEST™ (Thermo Fisher), pLenti6.2/V5-DEST™ (Thermo Fisher), pLKO.1 (Plasmid #10878 at Addgene), pLKO.3G (Plasmid #14748 at Addgene), pSico (Plasmid #11578 at Addgene), pLJM1-EGFP (Plasmid #19319 at Addgene), FUGW (Plasmid #14883 at Addgene), pLVTHM (Plasmid #12247 at Addgene), pLVUT-tTR-KRAB (Plasmid #11651 at Addgene), pLL3.7 (Plasmid #11795 at Addgene), pLB (Plasmid #11619 at Addgene), pWPXL (Plasmid #12257 at Addgene), pWPI (Plasmid #12254 at Addgene), EF.CMV.RFP (Plasmid #17619 at Addgene), pLenti CMV Puro DEST (Plasmid #17452 at Addgene), pLenti-puro (Plasmid #39481 at Addgene), pULTRA (Plasmid #24129 at Addgene), pLX301 (Plasmid #25895 at Addgene), pHIV-EGFP (Plasmid #21373 at Addgene), pLV-mCherry (Plasmid #36084 at Addgene), pLionII (Plasmid #1730 at Addgene), pInducer10-mir-RUP-PheS (Plasmid #44011 at Addgene). These vectors can be modified to be suitable for therapeutic use. For example, a selection marker (e.g., puro, EGFP, or mCherry) can be deleted or replaced with a second exogenous gene of interest. Further examples of lentiviral vectors are disclosed in U.S. Pat. Nos. 7,629,153, 7,198,950, 8,329,462, 6,863,884, 6,682,907, 7,745,179, 7,250,299, 5,994,136, 6,287,814, 6,013,516, 6,797,512, 6,544,771, 5,834,256, 6,958,226, 6,207,455, 6,531,123, and 6,352,694, and PCT Publication No. WO2017/091786.

Adenoviral Vectors

In certain embodiments, the viral vector can be an adenoviral vector. Adenoviruses are medium-sized (90-100 nm), non-enveloped (naked), icosahedral viruses composed of a nucleocapsid and a double-stranded linear DNA genome. The term "adenovirus" refers to any virus in the genus Adenoviridiae including, but not limited to, human, bovine, ovine, equine, canine, porcine, murine, and simian adenovirus subgenera. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

A human adenovirus can be used as the source of the adenoviral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serogroup or serotype. Adenoviral serotypes 1 through 51 are available from the American Type Culture Collection (ATCC, Manassas, Va.). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and PCT Publication Nos. WO1997/012986 and WO1998/053087.

Non-human adenovirus (e.g., ape, simian, avian, canine, ovine, or bovine adenoviruses) can be used to generate the adenoviral vector (i.e., as a source of the adenoviral genome for the adenoviral vector). For example, the adenoviral vector can be based on a simian adenovirus, including both new world and old world monkeys (see, e.g., Virus Taxonomy: VIIIth Report of the International Committee on Taxonomy of Viruses (2005)). A phylogeny analysis of adenoviruses that infect primates is disclosed in, e.g., Roy et al. (2009) PLoS PATHOG. 5(7):e1000503. A gorilla adenovirus can be used as the source of the adenoviral genome for the adenoviral vector. Gorilla adenoviruses and adenoviral vectors are described in, e.g., PCT Publication Nos.WO2013/052799, WO2013/052811, and WO2013/052832. The adenoviral vector can also comprise a combination of subtypes and thereby be a "chimeric" adenoviral vector.

The adenoviral vector can be replication-competent, conditionally replication-competent, or replication-deficient. A replication-competent adenoviral vector can replicate in typical host cells, i.e., cells typically capable of being infected by an adenovirus. A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., a promoter. Conditionally-replicating adenoviral vectors are further described in U.S. Pat. No. 5,998,205. A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

In some embodiments, the adenoviral vector is replication-deficient, such that the replication-deficient adenoviral vector requires complementation of at least one replication-essential gene function of one or more regions of the adenoviral genome for propagation (e.g., to form adenoviral vector particles). The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See, e.g., Morsy et al. (1998) PROC. NATL. ACAD. SCI. USA 95: 965-976, Chen et al. (1997) PROC. NATL. ACAD. SCI. USA 94: 1645-1650, and Kochanek et al. (1999) HUM. GENE THER. 10(15):2451-9. Examples of replication-deficient adenoviral vectors are disclosed in U.S. Pat. Nos. 5,837,511, 5,851,806, 5,994,106, 6,127,175, 6,482,616, and 7,195,896, and PCT Publication Nos. WO1994/028152, WO1995/002697, WO1995/016772, WO1995/034671, WO1996/022378, WO1997/012986, WO1997/021826, and WO2003/022311.

The replication-deficient adenoviral vector can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al. (1977) J. GEN. VIROL. 36: 59-72), PER.C6 cells (described in, e.g., PCT Publication No. WO1997/000326, and U.S. Pat. Nos. 5,994,128 and 6,033,908), and 293-ORF6 cells (described in, e.g., PCT Publication No. WO1995/034671 and Brough et al. (1997) J. VIROL. 71: 9206-9213). Other complementing cell lines to produce the replication-deficient adenoviral vector described herein include complementing cells that have been generated to propagate adenoviral vectors encoding transgenes whose expression inhibits viral growth in host cells (see, e.g., U.S. Patent Publication No. 2008/0233650). Additional complementing cells are described in, for example, U.S. Pat. Nos. 6,677,156 and 6,682,929, and PCT Publication No. WO2003/020879. Formulations for adenoviral vector-containing compositions are further described in, for example, U.S. Pat. Nos. 6,225,289, and 6,514,943, and PCT Publication No. WO2000/034444.

Additional exemplary adenoviral vectors, and/or methods for making or propagating adenoviral vectors are described in U.S. Pat. Nos. 5,559,099, 5,837,511, 5,846,782, 5,851,806, 5,994,106, 5,994,128, 5,965,541, 5,981,225, 6,040,174, 6,020,191, 6,083,716, 6,113,913, 6,303,362, 7,067,310, and 9,073,980.

Commercially available adenoviral vector systems include the ViraPower™ Adenoviral Expression System available from Thermo Fisher Scientific, the AdEasy™ adenoviral vector system available from Agilent Technologies, and the Adeno-X™ Expression System 3 available from Takara Bio USA, Inc.

Viral Vector Production

Methods for producing viral vectors are known in the art. Typically, a virus of interest is produced in a suitable host cell line using conventional techniques including culturing a transfected or infected host cell under suitable conditions so as to allow the production of infectious viral particles. Nucleic acids encoding viral genes and/or tRNAs can be incorporated into plasmids and introduced into host cells through conventional transfection or transformation techniques. Examples of host cells for production of disclosed viruses include human cell lines, such as HeLa, Hela-S3, HEK293, 911, A549, HER96, or PER-C6 cells. Specific production and purification conditions can vary depending upon the virus and the production system employed.

In certain embodiments, producer cells may be directly administered to a subject, however, in other embodiments, following production, infectious viral particles are recovered from the culture and optionally purified. Typical purification steps may include plaque purification, centrifugation, e.g., cesium chloride gradient centrifugation, clarification, enzymatic treatment, e.g., benzonase or protease treatment, chromatographic steps, e.g., ion exchange chromatography or filtration steps.

Pharmaceutical Compositions

For therapeutic use, a tRNA and/or expression vector preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (See Remington's Pharmaceutical Sciences, 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1: 10-29). In certain embodiments, the composition does not comprise a nanoparticle or an aminolipid delivery compound, e.g., as described in U.S. Patent Publication No. 2017/0354672. In certain embodiments, the tRNA or expression vector introduced into the cell or administered to the subject is not conjugated to or associated with another moiety, e.g., a carrier particle, e.g., an aminolipid particle. As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically, the moieties are attached either by one or more covalent bonds or by a mechanism that involves specific binding. Alternately, a sufficient number of weaker interactions can provide sufficient stability for moieties to remain physically associated.

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (-)-3-hydroxybutyric acid. Sustained release compositions may also include liposomes that can be prepared by any of several methods known in the art.

Pharmaceutical compositions containing a tRNA and/or expression vector disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a tRNA and/or expression vector is administered intrathecally. In certain embodiments, a tRNA and/or expression vector is administered by injection. Useful formulations can be prepared by methods known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

In general, any method of delivering a nucleic acid molecule can be adapted for use with a tRNA (see e.g., Akhtar et al. (1992) TRENDS CELL. BIOL. 2(5):139-144 and PCT Publication No. WO94/02595). The tRNA can be modified or alternatively delivered using a drug delivery system to prevent the rapid degradation of the tRNA by endo- and exo-nucleases in vivo. tRNA molecules can be modified by chemical conjugation to lipophilic groups such as cholesterol to enhance cellular uptake and prevent degradation. tRNA molecules can also be conjugated to or otherwise associated with an aptamer. A tRNA can also be delivered using drug delivery systems, such as a nanoparticle, a dendrimer, a polymer, liposomes, or a cationic delivery system. Positively charged cationic delivery systems facilitate binding of a tRNA molecule (negatively charged) and also enhance interactions at the negatively charged cell membrane to permit efficient uptake of a tRNA by the cell. Cationic lipids, dendrimers, or polymers can either be bound to the RNA, e.g., tRNA, or induced to form a vesicle or micelle (see e.g., Kim et al. (2008) JOURNAL OF CONTROLLED RELEASE 129(2):107-116) that encases the RNA. Methods for making and administering cationic-RNA complexes are well within the abilities of one skilled in the art (see, e.g., Sorensen et al. (2003) J. MOL. BIOL 327:761-766; Verma et al. (2003) CLIN. CANCER RES. 9:1291-1300; Arnold et al. (2007) J. HYPERTENS. 25:197-205). Some non-limiting examples of drug delivery systems useful for systemic delivery of RNAs, e.g., tRNAs include DOTAP (Sorensen et al. (2003) supra; Verma et al. (2003), supra), Oligofectamine, solid nucleic acid lipid particles (Zimmermann et al. (2006) NATURE 441:111-114), cardiolipin (Chien et al. (2005) CANCER GENE THER. 12:321-328; Pal et al. (2005) INT J. ONCOL. 26:1087-1091), polyethyleneimine (Bonnet et al. (2008) PHARM. RES. 25(12):2972-82; Aigner (2006) J. BIOMED. BIOTECHOL. 71659), Arg-Gly-Asp (RGD) peptides (Liu (2006) MOL. PHARM. 3:472-487), and polyamidoamines (Tomalia et al. (2007) BIOCHEM. SOC. TRANS. 35:61-67; Yoo et al. (1999) PHARM. RES. 16:1799-1804). In certain embodiments, a tRNA forms a complex with cyclodextrin for systemic administration. Methods for administration and pharmaceutical compositions of RNAs and cyclodextrins can be found in U.S. Pat. No. 7,427,605.

Pharmaceutical formulations can be sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In some embodiments, the pharmaceutical composition is administered subcutaneously and in other embodiments intravenously. Preparations for parenteral administration include sterile aqueous or non-aqueous solutions, suspensions, and emulsions.

Generally, a therapeutically effective amount of active component, for example, a tRNA and/or expression vector, is in the range of 0.1 mg/kg to 100 mg/kg, e.g., 1 mg/kg to 100 mg/kg, 1 mg/kg to 10 mg/kg. In certain embodiments, a therapeutically effective amount of a viral expression vector is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life, and the disease being treated. Examples of dosing frequencies are once per day, once per week and once every two weeks. In some embodiments, a route of administration is parenteral, e.g., intravenous infusion.

Therapeutic Uses

The compositions and methods disclosed herein can be used to treat a premature stop codon (PSC)-mediated disorder in a subject. As used herein, the term "PSC-mediated disorder" refers to a disorder that is mediated, enhanced or otherwise facilitated by or associated with a PSC in a gene. Examples of PSC-mediated disorders include β-thalassemia, Choroideremia (CHM), Cystic Fibrosis, Dravet Syndrome, Duchenne Muscular Dystrophy, Hurler Syndrome, KIF1A, a Lysosomal Storage Disease (e.g., Maroteaux-Lamy Syndrome, Niemann Pick Disease, and Sanfilippo Syndrome), Marfan Syndrome, Smith-Lemli-Opitz Syndrome, and Spinal Muscular Atrophy.

In some embodiments, the PSC-mediated disorder is selected from epilepsy disorders, epileptic encephalopathies, Dravet Syndrome, Lennox-Gastaut Syndrome, Kleefstra Syndrome, Duchenne Muscular Dystrophy; KCNQ2 Encephalopathy, SYNGAP1 Encephalopathy, Parkinson's with GBA, CDKL5, SLC6A1, BRMUTD, Sotos Syndrome, GLUT1 Deficiency Syndrome and any other PSC-mediated disorder associated with a central nervous system (CNS)-related disorder. In some embodiments, the PSC-mediated disorder is selected from epilepsy disorder or epileptic encephalopathies, including Dravet Syndrome and Lennox-Gastaut Syndrome.

In still other embodiments of any of the foregoing methods of treatment, the PSC-mediated disorder is selected 5q-syndrome, Adams-Oliver syndrome 1, Alagille syndrome 1, Autoimmune lymphoproliferative syndrome type 1A, Carney complex type I, CHARGE syndrome, Coffin-Siris Syndrome, Duane Syndrome, Cystic Fibrosis, Marfan Syndrome, Ehlers-Danlos Syndrome, Feingold Syndrome 1, Denys-Drash syndrome/Frasier Syndrome, DiGeorge Syndrome (TBX1-associated), Cleidocranial dysplasia, or any other non-CNS-related disorder not listed above.

In some embodiments, a method of treating a PSC-mediated disorder in a subject in need thereof includes administering to the subject an effective amount of a tRNA and/or expression vector, e.g., a tRNA and/or expression vector disclosed herein, either alone or in a combination with another therapeutic agent to treat the PSC-mediated disorder in the subject.

In certain embodiments, wherein the PSC-mediated disorder is Dravet syndrome, the method reduces seizure frequency, seizure severity, and/or cognitive impairment in the subject. For example, in certain embodiments, the method reduces seizure frequency in the subject by at least 10%, 20%, 30%, 40%, 50%, 60%, 70%, 80%, 90% or 100% over the period of, e.g., a day, a week, or a month. In certain embodiments, the method reduces seizure frequency by 50% over the period of, e.g., a day, a week, or a month.

The term "effective amount" as used herein refers to the amount of an active agent (e.g., tRNA or expression vector described herein) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive.

The delivery can be such that an effect of the first treatment delivered is still detectable when the second is delivered.

In certain embodiments, a method or composition described herein is administered in combination with one or more additional therapies, e.g., DIACOMIT® (stiripentol), EPIODOLEX® (cannabidiol), a ketogenic diet, ONFI® (clobazam), TOPAMAX® (topiramate), or valproic acid. For example, during the treatment of Dravet Syndrome, a method or composition described herein is administered in combination with one or more additional therapies, e.g., DIACOMIT® (stiripentol), EPIODOLEX® (cannabidiol), a ketogenic diet, ONFI® (clobazam), TOPAMAX® (topiramate), or valproic acid.

Throughout the description, where compositions are described as having, including, or comprising specific components, or where processes and methods are described as having, including, or comprising specific steps, it is contemplated that, additionally, there are compositions that consist essentially of, or consist of, the recited components, and that there are processes and methods that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition and/or a method described herein can be combined in a variety of ways without departing from the spirit and scope of the compositions and/or methods described herein, whether explicit or implicit herein. For example, where reference is made to a particular compound, that compound can be used in various embodiments of compositions and/or in methods described herein, unless otherwise understood from the context. In other words, within this application, embodiments have been described and depicted in a way that enables a clear and concise application to be written and drawn, but it is intended and will be appreciated that embodiments may be variously combined or separated without parting from the present teachings. For example, it will be appreciated that all features described and depicted herein can be applicable to all aspects of the composition(s) and method(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1

This examples describes arginine aminoacylated suppressor tRNAs that facilitate read-through of a premature stop codon (PSC) in a SCN1A transcript.

Figures 3, 4:
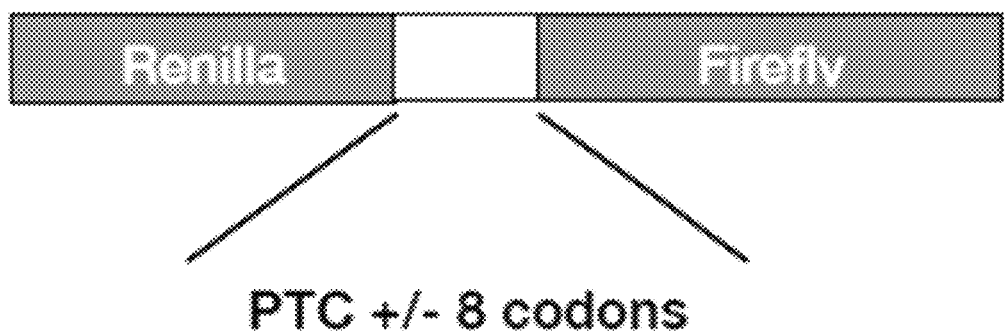
FIG. 3 is a schematic representation of a luciferase reporter construct which contains Renilla luciferase linked to Firefly luciferase via an intervening sequence containing a PSC+/−8 flanking codons.
FIG. 4 shows nucleotide sequences encoding Arg-TCA-1-1 (SEQ ID NO: 1), Arg-TCA-3-1 (SEQ ID NO: 2) and Arg-TCA-6-1 (SEQ ID NO: 3). Mutant TCA anticodons are identified in boxes.

Luciferase reporter constructs were synthesized based on SCN1A transcripts of two Dravet syndrome subjects containing a PSC (subject A and subject B). The reporter construct contained a nucleotide sequence encoding Renilla luciferase and a nucleotide sequence encoding Firefly luciferase linked by an intervening sequence. The intervening sequence contained the PSC and eight flanking codons from the SCN1A transcript of subject A (SEQ ID NO: 12) and subject B (SEQ ID NO: 13) (FIG. 3). The reporter constructs are hereafter referred to as the subject A and subject B reporter constructs. For each of the subject A and subject B reporter constructs, a control reported construct was synthesized that was the same except for a CGA (arginine) codon that was inserted in place of the PSC.

Suppressor tRNAs were derived from tRNA-Arginine genes (tRNA-Arg-TCG-1-1, tRNA-Arg-TCG-3-1, and tRNA-Arg-TCG-6-1). In each RNA, the TCG anticodon was mutated to TCA, producing tRNAs referred to as Arg-TCA-1-1 (SEQ ID NO: 1), Arg-TCA-3-1 (SEQ ID NO: 2) and Arg-TCA-6-1 (SEQ ID NO: 3). Arg-TCA-1-1 (SEQ ID NO: 1), Arg-TCA-3-1 (SEQ ID NO: 2) and Arg-TCA-6-1 (SEQ ID NO: 3) are depicted in FIG. 4, with the mutant TCA anticodon indicated.

Nucleotide sequences encoding the Arg-TCA-1-1 tRNA along with 200 base pairs (bp) of flanking genomic DNA sequence from the corresponding wild-type tRNA gene (SEQ ID NO: 5), the Arg-TCA-3-1 tRNA along with 200 bp of flanking genomic DNA sequence from the corresponding wild-type tRNA gene (SEQ ID NO: 6), and the Arg-TCA-6-1 tRNA along with 200 bp of flanking genomic DNA sequence from the corresponding wild-type tRNA gene (SEQ ID NO: 7) were cloned into pTRE-Tight (Clontech) using XhoI and PciI restriction enzyme sites, which resulted in removal of the Ptight, MCS, and SV40 poly A sequences.

HEK293 cells grown in DMEM with 10% FBS to 30-40% confluence were co-transfected with reporter constructs and the tRNAs using Effectene (Qiagen). Twenty-four hours later, cells were harvested and Firefly and Renilla luciferase activities were determined using the Dual-Luciferase® Reporter Assay System (Promega).

Figure 5A:
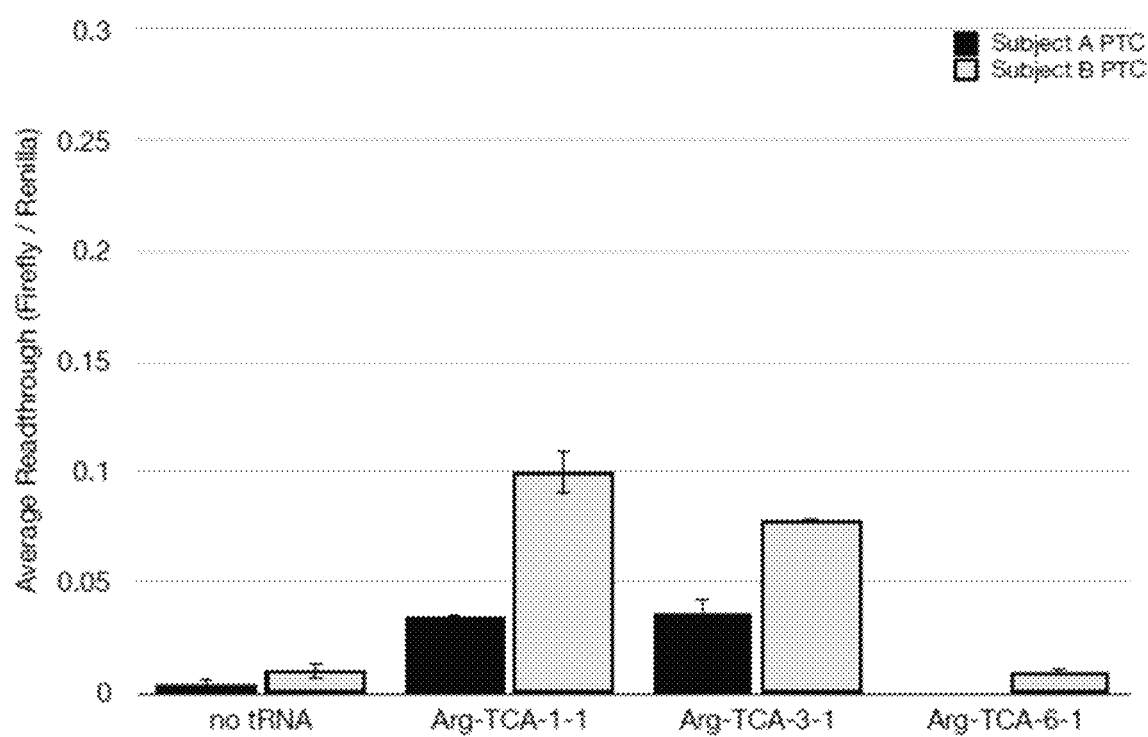
FIGS. 5A-5B are graphs indicating premature stop codon (PSC) read-through in HEK293 cells transfected with the indicated luciferase reporter construct and/or suppressor tRNA. Read-through of the PSC was calculated as the ratio of Firefly luciferase activity to Renilla luciferase activity (Firefly/Renilla). The average readthrough shown on the y-axis is the average readthrough of the PSC containing construct (Firefly/Renilla) divided by the average readthrough of the control CGA containing construct (Firefly/Renilla).

As shown in FIG. 5A, expression of the synthetic Arg-TCA-1-1 and Arg-TCA-3-1 suppressor tRNAs facilitated read-through of both the subject A and subject B reporter constructs.

In addition, Arg-TCG-1-1 was tested with varying flanking or regulatory sequences. A nucleotide sequence encoding the Arg-TCA-1-1 tRNAs along with (i) 46 bp of flanking genomic DNA sequence from the corresponding wild-type tRNA gene ("minimal"; SEQ ID NO: 8), (ii) an upstream U6 promoter plus 46 bp of flanking genomic DNA sequence from the corresponding wild-type tRNA gene ("U6P+minimal"; SEQ ID NO: 10) or (iii) 200 bp of flanking genomic DNA sequence from the corresponding wild-type tRNA gene ("+/−200"; SEQ ID NO: 5) was cloned into pTRE-Tight as described above.

Figures 5B, 6:
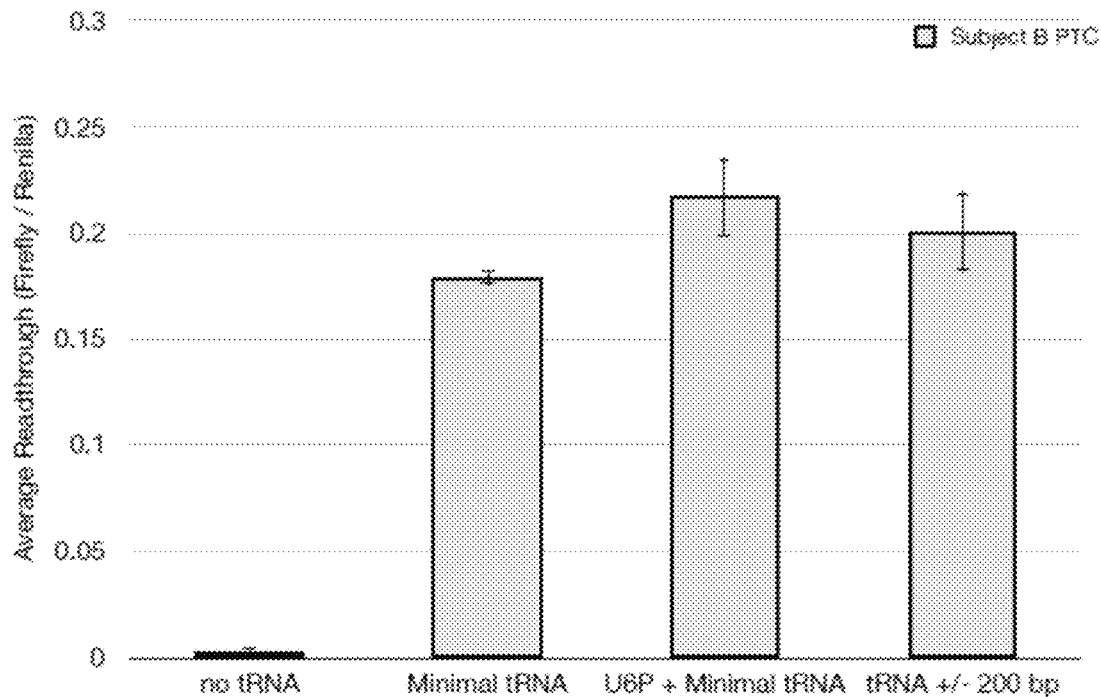
FIG. 6 shows nucleotide sequences encoding Gln-TTA-1-1 (SEQ ID NO: 16), Gln-TTA-2-1 (SEQ ID NO: 17) and Gln-TTA-3-1 (SEQ ID NO: 18). Mutant TTA anticodons are identified in boxes.

HEK-293 cells were co-transfected with the tRNA expressing constructs and the subject B luciferase reporter construct. Cell transfection, luminescence detection, and read-through calculation were performed as described above. As shown in FIG. 5B, expression of each of the minimal, U6P+minimal, and +/−200 bp tRNA-Arg-TCA-1-1 constructs facilitated read-through of the subject B reporter constructs.

Together, these results demonstrate that the described suppressor tRNAs can facilitate expression of SCN1A transcripts containing premature stop codons associated with Dravet syndrome.

Example 2

This example describes glutamine aminoacylated suppressor tRNAs that facilitate read-through of a premature stop codon (PSC) in a transcript.

Suppressor tRNAs are derived from tRNA-Glutamine genes (tRNA-Gln-TTG-1-1, tRNA-Gln-TTG-2-1, and tRNA-Gln-TTG-3-1). In each RNA, the TTG anticodon is mutated to TTA, producing tRNAs referred to as Gln-TTA-1-1 (SEQ ID NO: 16), Gln-TTA-2-1 (SEQ ID NO: 17) and Gln-TTA-3-1 (SEQ ID NO: 18). Gln-TTA-1-1 (SEQ ID NO: 16), Gln-TTA-2-1 (SEQ ID NO: 17) and Gln-TTA-3-1 (SEQ ID NO: 18) are depicted in FIG. 6, with the mutant TTA anticodon indicated.

Nucleotide sequences encoding the Gln-TTA-1-1 tRNA along with 200 base pairs (bp) of flanking genomic DNA sequence from the corresponding wild-type tRNA gene (SEQ ID NO: 19), the Gln-TTA-2-1 tRNA along with 200 bp of flanking genomic DNA sequence from the corresponding wild-type tRNA gene (SEQ ID NO: 20), and the Gln-TTA-3-1 tRNA along with 200 bp of flanking genomic DNA sequence from the corresponding wild-type tRNA gene (SEQ ID NO: 21) are cloned into pTRE-Tight (Clontech) using XhoI and PciI restriction enzyme sites, which results in removal of the Ptight, MCS, and SV40 poly A sequences.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Having described the invention, the following is claimed:

1. A method of treating Dravet syndrome in a subject in need thereof, the method comprising:
   administering to the subject an effective amount of a tRNA and/or an expression vector capable of expression of the tRNA, wherein the tRNA (i) comprises an anticodon that hybridizes to the premature stop codon, and (ii) is capable of being aminoacylated with an amino acid, thereby to treat the Dravet syndrome in the subject, wherein the subject has an SCN1A gene with premature stop codon mutation selected from c.664C>T, c.1129C>T, c.1492A>T, c.1624C>T, c.1738C>T, c.1837C>T, c.2134C>T, c.2593C>T, c.3637C>T, c.3733C>T, c.3985C>T, c.4573C>T, c.5656C>T, and c.5734C>T; and wherein the tRNA comprises a nucleotide sequence selected from SEQ ID NO: 1, SEQ ID NO: 2, SEQ ID NO: 3, SEQ ID NO: 16, SEQ ID NO: 17, and SEQ ID NO: 18.

2. The method of claim 1, wherein the SCN1A gene is caused by a mutation selected from c.1738C>T and c.3985C>T.

3. The method of claim 1, wherein the amino acid is selected from serine, leucine, glutamine, and arginine.

4. The method of claim 1, wherein the tRNA comprises the nucleotide sequence selected from SEQ ID NO: 1, SEQ ID NO: 2, and SEQ ID NO: 3.

5. The method of claim 1, wherein the expression vector comprises a nucleotide sequence selected from SEQ ID NO: 5, SEQ ID NO: 6, SEQ ID NO: 8, SEQ ID NO: 9, SEQ ID NO: 10, SEQ ID NO: 11, SEQ ID NO: 19, SEQ ID NO: 20, and SEQ ID NO: 21.

6. The method of claim 1, wherein the expression vector comprises a nucleotide sequence selected from SEQ ID NO: 5, SEQ ID NO: 8, and SEQ ID NO: 10.

* * * * *

UNITED STATES PATENT AND TRADEMARK OFFICE
CERTIFICATE OF CORRECTION

PATENT NO. : 10,905,778 B2
APPLICATION NO. : 16/665526
DATED : February 2, 2021
INVENTOR(S) : Jeffery M. Coller et al.

Page 1 of 1

It is certified that error appears in the above-identified patent and that said Letters Patent is hereby corrected as shown below:

On the Title Page

Item (72) reads:
"Jeffery M. Coller, Cleveland, OH (US); Thomas Sweet, Cleveland, OH (US)"

Should read:
--Jeffery M. Coller, Cleveland, OH (US); Thomas Sweet, Cleveland, OH (US); Harvey Lodish, Cambridge, MA (US)--

Signed and Sealed this
Third Day of August, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 21

<210> SEQ ID NO 1
<211> LENGTH: 73
<212> TYPE: DNA
<213> ORGANISM: Artificial Sequence
<220> FEATURE:
<223> OTHER INFORMATION: Synthetic Construct

<400> SEQUENCE: 1
ggccgcgtgg cctaatggat aaggcgtctg acttcagatc agaagattgc aggttcgagt      60
cctgccgcgg tcg                                                         73

<210> SEQ ID NO 2
<211> LENGTH: 73
<212> TYPE: DNA
<213> ORGANISM: Artificial Sequence
<220> FEATURE:
<223> OTHER INFORMATION: Synthetic Construct

<400> SEQUENCE: 2
gaccgcgtgg cctaatggat aaggcgtctg acttcagatc agaagattga gggttcgagt      60
cccttcgtgg tcg                                                         73

<210> SEQ ID NO 3
<211> LENGTH: 73
<212> TYPE: DNA
<213> ORGANISM: Artificial Sequence
<220> FEATURE:
```

<223> OTHER INFORMATION: Synthetic Construct

<400> SEQUENCE: 3
ggccgtgtgg cctaatggat aaggcgtctg acttcagatc aaaagattgc aggtttgagt    60
tctgccacgg tcg    73

<210> SEQ ID NO 4
<211> LENGTH: 2009
<212> TYPE: PRT
<213> ORGANISM: Homo sapiens

<400> SEQUENCE: 4

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

-continued

Gly Asn Ser Ser Asp Ala Gly Gln Cys Pro Glu Gly Tyr Met Cys Val
        340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
        370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Gln Ala Ala Thr Ala
            450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
        610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
        690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro

```
                755            760            765
    Phe Val Asp Leu Ala Ile Thr Ile Cys Ile Val Leu Asn Thr Leu Phe
    770            775            780

Met Ala Met Glu His Tyr Pro Met Thr Asp His Phe Asn Asn Val Leu
785            790            795            800

Thr Val Gly Asn Leu Val Phe Thr Gly Ile Phe Thr Ala Glu Met Phe
                805            810            815

Leu Lys Ile Ile Ala Met Asp Pro Tyr Tyr Tyr Phe Gln Glu Gly Trp
                820            825            830

Asn Ile Phe Asp Gly Phe Ile Val Thr Leu Ser Leu Val Glu Leu Gly
                835            840            845

Leu Ala Asn Val Glu Gly Leu Ser Val Leu Arg Ser Phe Arg Leu Leu
    850            855            860

Arg Val Phe Lys Leu Ala Lys Ser Trp Pro Thr Leu Asn Met Leu Ile
865            870            875            880

Lys Ile Ile Gly Asn Ser Val Gly Ala Leu Gly Asn Leu Thr Leu Val
                885            890            895

Leu Ala Ile Ile Val Phe Ile Phe Ala Val Val Gly Met Gln Leu Phe
                900            905            910

Gly Lys Ser Tyr Lys Asp Cys Val Cys Lys Ile Ala Ser Asp Cys Gln
                915            920            925

Leu Pro Arg Trp His Met Asn Asp Phe Phe His Ser Phe Leu Ile Val
    930            935            940

Phe Arg Val Leu Cys Gly Glu Trp Ile Glu Thr Met Trp Asp Cys Met
945            950            955            960

Glu Val Ala Gly Gln Ala Met Cys Leu Thr Val Phe Met Met Val Met
                965            970            975

Val Ile Gly Asn Leu Val Val Leu Asn Leu Phe Leu Ala Leu Leu Leu
                980            985            990

Ser Ser Phe Ser Ala Asp Asn Leu Ala Ala Thr Asp Asp Asp Asn Glu
                995            1000           1005

Met Asn Asn Leu Gln Ile Ala Val Asp Arg Met His Lys Gly Val
        1010           1015           1020

Ala Tyr Val Lys Arg Lys Ile Tyr Glu Phe Ile Gln Gln Ser Phe
        1025           1030           1035

Ile Arg Lys Gln Lys Ile Leu Asp Glu Ile Lys Pro Leu Asp Asp
        1040           1045           1050

Leu Asn Asn Lys Lys Asp Ser Cys Met Ser Asn His Thr Ala Glu
        1055           1060           1065

Ile Gly Lys Asp Leu Asp Tyr Leu Lys Asp Val Asn Gly Thr Thr
        1070           1075           1080

Ser Gly Ile Gly Thr Gly Ser Ser Val Glu Lys Tyr Ile Ile Asp
        1085           1090           1095

Glu Ser Asp Tyr Met Ser Phe Ile Asn Asn Pro Ser Leu Thr Val
        1100           1105           1110

Thr Val Pro Ile Ala Val Gly Glu Ser Asp Phe Glu Asn Leu Asn
        1115           1120           1125

Thr Glu Asp Phe Ser Ser Glu Ser Asp Leu Glu Glu Ser Lys Glu
        1130           1135           1140

Lys Leu Asn Glu Ser Ser Ser Ser Ser Glu Gly Ser Thr Val Asp
        1145           1150           1155

Ile Gly Ala Pro Val Glu Glu Gln Pro Val Val Glu Pro Glu Glu
        1160           1165           1170
```

-continued

```
Thr Leu Glu Pro Glu Ala Cys Phe Thr Glu Gly Cys Val Gln Arg
1175                1180                1185

Phe Lys Cys Cys Gln Ile Asn Val Glu Gly Arg Gly Lys Gln
1190                1195                1200

Trp Trp Asn Leu Arg Arg Thr Cys Phe Arg Ile Val Glu His Asn
1205                1210                1215

Trp Phe Glu Thr Phe Ile Val Phe Met Ile Leu Leu Ser Ser Gly
1220                1225                1230

Ala Leu Ala Phe Glu Asp Ile Tyr Ile Asp Gln Arg Lys Thr Ile
1235                1240                1245

Lys Thr Met Leu Glu Tyr Ala Asp Lys Val Phe Thr Tyr Ile Phe
1250                1255                1260

Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Glu Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560
```

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
1640                1645                1650

Lys Gly Ile Arg Thr Leu Leu Phe Ala Leu Met Met Ser Leu Pro
1655                1660                1665

Ala Leu Phe Asn Ile Gly Leu Leu Leu Phe Leu Val Met Phe Ile
1670                1675                1680

Tyr Ala Ile Phe Gly Met Ser Asn Phe Ala Tyr Val Lys Arg Glu
1685                1690                1695

Val Gly Ile Asp Asp Met Phe Asn Phe Glu Thr Phe Gly Asn Ser
1700                1705                1710

Met Ile Cys Leu Phe Gln Ile Thr Thr Ser Ala Gly Trp Asp Gly
1715                1720                1725

Leu Leu Ala Pro Ile Leu Asn Ser Lys Pro Pro Asp Cys Asp Pro
1730                1735                1740

Asn Lys Val Asn Pro Gly Ser Ser Val Lys Gly Asp Cys Gly Asn
1745                1750                1755

Pro Ser Val Gly Ile Phe Phe Phe Val Ser Tyr Ile Ile Ile Ser
1760                1765                1770

Phe Leu Val Val Val Asn Met Tyr Ile Ala Val Ile Leu Glu Asn
1775                1780                1785

Phe Ser Val Ala Thr Glu Glu Ser Ala Glu Pro Leu Ser Glu Asp
1790                1795                1800

Asp Phe Glu Met Phe Tyr Glu Val Trp Glu Lys Phe Asp Pro Asp
1805                1810                1815

Ala Thr Gln Phe Met Glu Phe Glu Lys Leu Ser Gln Phe Ala Ala
1820                1825                1830

Ala Leu Glu Pro Pro Leu Asn Leu Pro Gln Pro Asn Lys Leu Gln
1835                1840                1845

Leu Ile Ala Met Asp Leu Pro Met Val Ser Gly Asp Arg Ile His
1850                1855                1860

Cys Leu Asp Ile Leu Phe Ala Phe Thr Lys Arg Val Leu Gly Glu
1865                1870                1875

Ser Gly Glu Met Asp Ala Leu Arg Ile Gln Met Glu Glu Arg Phe
1880                1885                1890

Met Ala Ser Asn Pro Ser Lys Val Ser Tyr Gln Pro Ile Thr Thr
1895                1900                1905

Thr Leu Lys Arg Lys Gln Glu Glu Val Ser Ala Val Ile Ile Gln
1910                1915                1920

Arg Ala Tyr Arg Arg His Leu Leu Lys Arg Thr Val Lys Gln Ala
1925                1930                1935

Ser Phe Thr Tyr Asn Lys Asn Lys Ile Lys Gly Gly Ala Asn Leu
1940                1945                1950

Leu Ile Lys Glu Asp Met Ile Ile Asp Arg Ile Asn Glu Asn Ser

Ile Thr Glu Lys Thr Asp Leu Thr Met Ser Thr Ala Ala Cys Pro
1970 1975 1980

Pro Ser Tyr Asp Arg Val Thr Lys Pro Ile Val Glu Lys His Glu
1985 1990 1995

Gln Glu Gly Lys Asp Glu Lys Ala Lys Gly Lys
2000 2005

<210> SEQ ID NO 5
<211> LENGTH: 473
<212> TYPE: DNA
<213> ORGANISM: Artificial Sequence
<220> FEATURE:
<223> OTHER INFORMATION: Synthetic Construct

<400> SEQUENCE: 5

| | | | | | | |
|---|---|---|---|---|---|---|
| gcgcgaccaa | taggagggcc | gccaatggag | cggtccgccc | gcgggggag | aaggggact | 60 |
| tctgggtggg | ctctccctgc | ggaacgcgcg | aaccaaaggc | caacctcccc | ttctcaagga | 120 |
| gcaggtggat | tggtcccgag | ctagctggtg | ggcggaggtg | acgttttat | aagttgctca | 180 |
| agagacggta | acaaccgacg | ggccgcgtgg | cctaatggat | aaggcgtctg | acttcagatc | 240 |
| agaagattgc | aggttcgagt | cctgccgcgg | tcgaagggag | gttatgatta | acttttagtt | 300 |
| tattcctccc | tcaggaacga | agtattggga | caatgtgaac | gtagtcgccg | ccgattccca | 360 |
| ccgcacttca | aagatgtggg | aacgccaaga | tccgcggaag | taaccacgcc | cagcaagtcc | 420 |
| ctgcgagatt | gcccgcctac | gtgtctcagc | ggaggcacat | ttctaaaatg | tac | 473 |

<210> SEQ ID NO 6
<211> LENGTH: 473
<212> TYPE: DNA
<213> ORGANISM: Artificial Sequence
<220> FEATURE:
<223> OTHER INFORMATION: Synthetic Construct

<400> SEQUENCE: 6

| | | | | | | |
|---|---|---|---|---|---|---|
| cgcggtcgca | attcccaggg | aggctcagag | actagtccag | gtgccgctcc | gctcggggt | 60 |
| gactaggcgg | gcggctgggg | ccagaggaag | ggtgagcgct | tcgctcaaca | ggcggccagg | 120 |
| gtgcgagcag | tgaagctgcg | gcacgccgga | gcgtttaatg | ccatcaaat | tggcctctct | 180 |
| aggaggtagc | tgcagccgga | gaccgcgtgg | cctaatggat | aaggcgtctg | acttcagatc | 240 |
| agaagattga | gggttcgagt | cccttcgtgg | tcggaacgtt | ttaatccctg | caactataat | 300 |
| cttccctccc | ttgttttaga | cccagaaacg | cctcccaatc | cctccacacc | gcggctcccg | 360 |
| ggatccgaag | ctggggagct | gcttctgtcc | aatcaggctt | tgcatcccgg | gacgcttccg | 420 |
| gttatggcgt | cattatgcag | ccagggtaag | tagggcccca | tttcttgttg | tct | 473 |

<210> SEQ ID NO 7
<211> LENGTH: 473
<212> TYPE: DNA
<213> ORGANISM: Artificial Sequence
<220> FEATURE:
<223> OTHER INFORMATION: Synthetic Construct

<400> SEQUENCE: 7

| | | | | | | |
|---|---|---|---|---|---|---|
| aggcagccac | atgggagtc | cacactggga | agtggaagcc | tggggaaccc | taggtaaagg | 60 |
| tggcctgcct | gatgcaggat | ttacaatgtg | agctggtttt | tctctatctt | aggaagagaa | 120 |
| gaggaaaact | ttctgctaat | gttatcggtg | gaggccatcc | aggctcttgg | cattttgaac | 180 |

```
aaagacttgg ccaaccagct ggccgtgtgg cctaatggat aaggcgtctg acttcagatc    240
aaaagattgc aggtttgagt tctgccacgg tcgtggaggg gttatatttt gttgggtgcg    300
gtggcttatg cctgtaatcc cagcatcttg ggaggccgag gaaagcggat cacctgaggt    360
cgggagtttg aggccagcct ggccaacatg gagaaacccc atctctacta aaaatacaaa    420
attagccggg cgtggtggcg catgcctgta atcccagcta ctcggtaggc tca           473
```

<210> SEQ ID NO 8
<211> LENGTH: 165
<212> TYPE: DNA
<213> ORGANISM: Artificial Sequence
<220> FEATURE:
<223> OTHER INFORMATION: Synthetic Construct

<400> SEQUENCE: 8

```
gaggtgacgt ttttataagt tgctcaagag acggtaacaa ccgacgggcc gcgtggccta     60
atggataagg cgtctgactt cagatcagaa gattgcaggt tcgagtcctg ccgcggtcga    120
agggaggtta tgattaactt ttagtttatt cctccctcag gaacg                    165
```

<210> SEQ ID NO 9
<211> LENGTH: 165
<212> TYPE: DNA
<213> ORGANISM: Artificial Sequence
<220> FEATURE:
<223> OTHER INFORMATION: Synthetic Construct

<400> SEQUENCE: 9

```
ttaatggcca tcaaattggc ctctctagga ggtagctgca gccggagacc gcgtggccta     60
atggataagg cgtctgactt cagatcagaa gattgagggt tcgagtccct tcgtggtcgg    120
aacgttttaa tccctgcaac tataatcttc cctcccttgt tttag                    165
```

<210> SEQ ID NO 10
<211> LENGTH: 389
<212> TYPE: DNA
<213> ORGANISM: Artificial Sequence
<220> FEATURE:
<223> OTHER INFORMATION: Synthetic Construct

<400> SEQUENCE: 10

```
cgagggccta tttcccatga ttccttcata tttgcatata cgatacaagg ctgttagaga     60
gataattaga attaatttga ctgtaaacac aaagatatta gtacaaaata cgtgacgtag    120
aaagtaataa tttcttgggt agtttgcagt tttaaaatta tgttttaaaa tggactatca    180
tatgcttacc gtaacttgaa agtatttcga tttcttggct ttatatatct tgtggaaagg    240
acgggcggag ggagacggta acaaccgacg ggccgcgtgg cctaatggat aaggcgtctg    300
acttcagatc agaagattgc aggttcgagt cctgccgcgg tcgaagggag gttatgatta    360
acttttagtt tattcctccc tcaggaacg                                      389
```

<210> SEQ ID NO 11
<211> LENGTH: 389
<212> TYPE: DNA
<213> ORGANISM: Artificial Sequence
<220> FEATURE:
<223> OTHER INFORMATION: Synthetic Construct

<400> SEQUENCE: 11

```
cgagggccta tttcccatga ttccttcata tttgcatata cgatacaagg ctgttagaga     60
gataattaga attaatttga ctgtaaacac aaagatatta gtacaaaata cgtgacgtag    120
```

-continued

```
aaagtaataa tttcttgggt agtttgcagt tttaaaatta tgttttaaaa tggactatca    180
tatgcttacc gtaacttgaa agtatttcga tttcttggct ttatatatct tgtggaaagg    240
acgggcggag gggaggtagc tgcagccgga gaccgcgtgg cctaatggat aaggcgtctg    300
acttcagatc agaagattga gggttcgagt cccttcgtgg tcggaacgtt ttaatccctg    360
caactataat cttccctccc ttgttttag                                       389
```

<210> SEQ ID NO 12
<211> LENGTH: 51
<212> TYPE: DNA
<213> ORGANISM: Artificial Sequence
<220> FEATURE:
<223> OTHER INFORMATION: Synthetic Construct

<400> SEQUENCE: 12

```
acaagccttt tcagctttag agggtgagca aaggatgtgg gatctgagaa c             51
```

<210> SEQ ID NO 13
<211> LENGTH: 51
<212> TYPE: DNA
<213> ORGANISM: Artificial Sequence
<220> FEATURE:
<223> OTHER INFORMATION: Synthetic Construct

<400> SEQUENCE: 13

```
ctgagacctc taagagcctt atcttgattt gaagggatga gggtggttgt g             51
```

<210> SEQ ID NO 14
<211> LENGTH: 1998
<212> TYPE: PRT
<213> ORGANISM: Homo sapiens

<400> SEQUENCE: 14

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Glu Asn Gly
            35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190
```

```
Leu Asp Phe Thr Val Ile Thr Phe Ala Tyr Val Thr Glu Phe Val Asp
            195                 200                 205

Leu Gly Asn Val Ser Ala Leu Arg Thr Phe Arg Val Leu Arg Ala Leu
            210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
            275                 280                 285

Glu His Ser Ile Glu Lys Asn Ile Thr Val Asn Tyr Asn Gly Thr Leu
            290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
            370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Ala Ala Thr Ala
450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
```

```
                610               615                620
Thr Ser Arg Ser Ser Arg Met Leu Ala Val Phe Pro Ala Asn Gly Lys
625                 630                635                640

Met His Ser Thr Val Asp Cys Asn Gly Val Val Ser Leu Val Gly Gly
                    645                650                655

Pro Ser Val Pro Thr Ser Pro Val Gly Gln Leu Leu Pro Glu Gly Thr
                660                665                670

Thr Thr Glu Thr Glu Met Arg Lys Arg Arg Ser Ser Ser Phe His Val
            675                680                685

Ser Met Asp Phe Leu Glu Asp Pro Ser Gln Arg Gln Arg Ala Met Ser
690                 695                700

Ile Ala Ser Ile Leu Thr Asn Thr Val Glu Glu Leu Glu Glu Ser Arg
705                 710                715                720

Gln Lys Cys Pro Pro Cys Trp Tyr Lys Phe Ser Asn Ile Phe Leu Ile
                725                730                735

Trp Asp Cys Ser Pro Tyr Trp Leu Lys Val Lys His Val Val Asn Leu
                740                745                750

Val Val Met Asp Pro Phe Val Asp Leu Ala Ile Thr Ile Cys Ile Val
            755                760                765

Leu Asn Thr Leu Phe Met Ala Met Glu His Tyr Pro Met Thr Asp His
770                 775                780

Phe Asn Asn Val Leu Thr Val Gly Asn Leu Val Phe Thr Gly Ile Phe
785                 790                795                800

Thr Ala Glu Met Phe Leu Lys Ile Ile Ala Met Asp Pro Tyr Tyr Tyr
                805                810                815

Phe Gln Glu Gly Trp Asn Ile Phe Asp Gly Phe Ile Val Thr Leu Ser
                820                825                830

Leu Val Glu Leu Gly Leu Ala Asn Val Glu Gly Leu Ser Val Leu Arg
            835                840                845

Ser Phe Arg Leu Leu Arg Val Phe Lys Leu Ala Lys Ser Trp Pro Thr
850                 855                860

Leu Asn Met Leu Ile Lys Ile Ile Gly Asn Ser Val Gly Ala Leu Gly
865                 870                875                880

Asn Leu Thr Leu Val Leu Ala Ile Ile Val Phe Ile Phe Ala Val Val
                885                890                895

Gly Met Gln Leu Phe Gly Lys Ser Tyr Lys Asp Cys Val Cys Lys Ile
                900                905                910

Ala Ser Asp Cys Gln Leu Pro Arg Trp His Met Asn Asp Phe Phe His
            915                920                925

Ser Phe Leu Ile Val Phe Arg Val Leu Cys Gly Glu Trp Ile Glu Thr
930                 935                940

Met Trp Asp Cys Met Glu Val Ala Gly Gln Ala Met Cys Leu Thr Val
945                 950                955                960

Phe Met Met Val Met Val Ile Gly Asn Leu Val Val Leu Asn Leu Phe
                965                970                975

Leu Ala Leu Leu Leu Ser Ser Phe Ser Ala Asp Asn Leu Ala Ala Thr
            980                985                990

Asp Asp Asp Asn Glu Met Asn Asn Leu Gln Ile Ala Val Asp Arg Met
            995                1000                1005

His Lys Gly Val Ala Tyr Val Lys Arg Lys Ile Tyr Glu Phe Ile
    1010                1015                1020

Gln Gln Ser Phe Ile Arg Lys Gln Lys Ile Leu Asp Glu Ile Lys
    1025                1030                1035
```

```
Pro Leu Asp Asp Leu Asn Asn Lys Lys Asp Ser Cys Met Ser Asn
    1040            1045            1050

His Thr Ala Glu Ile Gly Lys Asp Leu Asp Tyr Leu Lys Asp Val
    1055            1060            1065

Asn Gly Thr Thr Ser Gly Ile Gly Thr Gly Ser Ser Val Glu Lys
    1070            1075            1080

Tyr Ile Ile Asp Glu Ser Asp Tyr Met Ser Phe Ile Asn Asn Pro
    1085            1090            1095

Ser Leu Thr Val Thr Val Pro Ile Ala Val Gly Glu Ser Asp Phe
    1100            1105            1110

Glu Asn Leu Asn Thr Glu Asp Phe Ser Ser Glu Ser Asp Leu Glu
    1115            1120            1125

Glu Ser Lys Glu Lys Leu Asn Glu Ser Ser Ser Ser Ser Glu Gly
    1130            1135            1140

Ser Thr Val Asp Ile Gly Ala Pro Val Glu Glu Gln Pro Val Val
    1145            1150            1155

Glu Pro Glu Glu Thr Leu Glu Pro Glu Ala Cys Phe Thr Glu Gly
    1160            1165            1170

Cys Val Gln Arg Phe Lys Cys Cys Gln Ile Asn Val Glu Glu Gly
    1175            1180            1185

Arg Gly Lys Gln Trp Trp Asn Leu Arg Arg Thr Cys Phe Arg Ile
    1190            1195            1200

Val Glu His Asn Trp Phe Glu Thr Phe Ile Val Phe Met Ile Leu
    1205            1210            1215

Leu Ser Ser Gly Ala Leu Ala Phe Glu Asp Ile Tyr Ile Asp Gln
    1220            1225            1230

Arg Lys Thr Ile Lys Thr Met Leu Glu Tyr Ala Asp Lys Val Phe
    1235            1240            1245

Thr Tyr Ile Phe Ile Leu Glu Met Leu Leu Lys Trp Val Ala Tyr
    1250            1255            1260

Gly Tyr Gln Thr Tyr Phe Thr Asn Ala Trp Cys Trp Leu Asp Phe
    1265            1270            1275

Leu Ile Val Asp Val Ser Leu Val Ser Leu Thr Ala Asn Ala Leu
    1280            1285            1290

Gly Tyr Ser Glu Leu Gly Ala Ile Lys Ser Leu Arg Thr Leu Arg
    1295            1300            1305

Ala Leu Arg Pro Leu Arg Ala Leu Ser Arg Phe Glu Gly Met Arg
    1310            1315            1320

Val Val Val Asn Ala Leu Leu Gly Ala Ile Pro Ser Ile Met Asn
    1325            1330            1335

Val Leu Leu Val Cys Leu Ile Phe Trp Leu Ile Phe Ser Ile Met
    1340            1345            1350

Gly Val Asn Leu Phe Ala Gly Lys Phe Tyr His Cys Ile Asn Thr
    1355            1360            1365

Thr Thr Gly Asp Arg Phe Asp Ile Glu Asp Val Asn Asn His Thr
    1370            1375            1380

Asp Cys Leu Lys Leu Ile Glu Arg Asn Glu Thr Ala Arg Trp Lys
    1385            1390            1395

Asn Val Lys Val Asn Phe Asp Asn Val Gly Phe Gly Tyr Leu Ser
    1400            1405            1410

Leu Leu Gln Val Ala Thr Phe Lys Gly Trp Met Asp Ile Met Tyr
    1415            1420            1425
```

```
Ala Ala Val Asp Ser Arg Asn Val Glu Leu Gln Pro Lys Tyr Glu
1430                1435                1440

Glu Ser Leu Tyr Met Tyr Leu Tyr Phe Val Ile Phe Ile Ile Phe
1445                1450                1455

Gly Ser Phe Phe Thr Leu Asn Leu Phe Ile Gly Val Ile Ile Asp
1460                1465                1470

Asn Phe Asn Gln Gln Lys Lys Lys Phe Gly Gly Gln Asp Ile Phe
1475                1480                1485

Met Thr Glu Glu Gln Lys Lys Tyr Tyr Asn Ala Met Lys Lys Leu
1490                1495                1500

Gly Ser Lys Lys Pro Gln Lys Pro Ile Pro Arg Pro Gly Asn Lys
1505                1510                1515

Phe Gln Gly Met Val Phe Asp Phe Val Thr Arg Gln Val Phe Asp
1520                1525                1530

Ile Ser Ile Met Ile Leu Ile Cys Leu Asn Met Val Thr Met Met
1535                1540                1545

Val Glu Thr Asp Asp Gln Ser Glu Tyr Val Thr Thr Ile Leu Ser
1550                1555                1560

Arg Ile Asn Leu Val Phe Ile Val Leu Phe Thr Gly Glu Cys Val
1565                1570                1575

Leu Lys Leu Ile Ser Leu Arg His Tyr Tyr Phe Thr Ile Gly Trp
1580                1585                1590

Asn Ile Phe Asp Phe Val Val Val Ile Leu Ser Ile Val Gly Met
1595                1600                1605

Phe Leu Ala Glu Leu Ile Glu Lys Tyr Phe Val Ser Pro Thr Leu
1610                1615                1620

Phe Arg Val Ile Arg Leu Ala Arg Ile Gly Arg Ile Leu Arg Leu
1625                1630                1635

Ile Lys Gly Ala Lys Gly Ile Arg Thr Leu Leu Phe Ala Leu Met
1640                1645                1650

Met Ser Leu Pro Ala Leu Phe Asn Ile Gly Leu Leu Leu Phe Leu
1655                1660                1665

Val Met Phe Ile Tyr Ala Ile Phe Gly Met Ser Asn Phe Ala Tyr
1670                1675                1680

Val Lys Arg Glu Val Gly Ile Asp Asp Met Phe Asn Phe Glu Thr
1685                1690                1695

Phe Gly Asn Ser Met Ile Cys Leu Phe Gln Ile Thr Thr Ser Ala
1700                1705                1710

Gly Trp Asp Gly Leu Leu Ala Pro Ile Leu Asn Ser Lys Pro Pro
1715                1720                1725

Asp Cys Asp Pro Asn Lys Val Asn Pro Gly Ser Ser Val Lys Gly
1730                1735                1740

Asp Cys Gly Asn Pro Ser Val Gly Ile Phe Phe Val Ser Tyr
1745                1750                1755

Ile Ile Ile Ser Phe Leu Val Val Val Asn Met Tyr Ile Ala Val
1760                1765                1770

Ile Leu Glu Asn Phe Ser Val Ala Thr Glu Glu Ser Ala Glu Pro
1775                1780                1785

Leu Ser Glu Asp Asp Phe Glu Met Phe Tyr Glu Val Trp Glu Lys
1790                1795                1800

Phe Asp Pro Asp Ala Thr Gln Phe Met Glu Phe Glu Lys Leu Ser
1805                1810                1815

Gln Phe Ala Ala Ala Leu Glu Pro Pro Leu Asn Leu Pro Gln Pro
```

Asn Lys Leu Gln Leu Ile Ala Met Asp Leu Pro Met Val Ser Gly
    1835                1840                1845

Asp Arg Ile His Cys Leu Asp Ile Leu Phe Ala Phe Thr Lys Arg
    1850                1855                1860

Val Leu Gly Glu Ser Gly Glu Met Asp Ala Leu Arg Ile Gln Met
    1865                1870                1875

Glu Glu Arg Phe Met Ala Ser Asn Pro Ser Lys Val Ser Tyr Gln
    1880                1885                1890

Pro Ile Thr Thr Thr Leu Lys Arg Lys Gln Glu Val Ser Ala
    1895                1900                1905

Val Ile Ile Gln Arg Ala Tyr Arg Arg His Leu Leu Lys Arg Thr
    1910                1915                1920

Val Lys Gln Ala Ser Phe Thr Tyr Asn Lys Asn Lys Ile Lys Gly
    1925                1930                1935

Gly Ala Asn Leu Leu Ile Lys Glu Asp Met Ile Ile Asp Arg Ile
    1940                1945                1950

Asn Glu Asn Ser Ile Thr Glu Lys Thr Asp Leu Thr Met Ser Thr
    1955                1960                1965

Ala Ala Cys Pro Pro Ser Tyr Asp Arg Val Thr Lys Pro Ile Val
    1970                1975                1980

Glu Lys His Glu Gln Glu Gly Lys Asp Glu Lys Ala Lys Gly Lys
    1985                1990                1995

<210> SEQ ID NO 15
<211> LENGTH: 1981
<212> TYPE: PRT
<213> ORGANISM: Homo sapiens

<400> SEQUENCE: 15

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

```
Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Ala Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
```

```
               610                 615                 620
Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Gly Thr Thr
                645                 650                 655

Thr Glu Thr Glu Met Arg Lys Arg Arg Ser Ser Ser Phe His Val Ser
            660                 665                 670

Met Asp Phe Leu Glu Asp Pro Ser Gln Arg Gln Arg Ala Met Ser Ile
        675                 680                 685

Ala Ser Ile Leu Thr Asn Thr Val Glu Glu Leu Glu Glu Ser Arg Gln
690                 695                 700

Lys Cys Pro Pro Cys Trp Tyr Lys Phe Ser Asn Ile Phe Leu Ile Trp
705                 710                 715                 720

Asp Cys Ser Pro Tyr Trp Leu Lys Val Lys His Val Val Asn Leu Val
                725                 730                 735

Val Met Asp Pro Phe Val Asp Leu Ala Ile Thr Ile Cys Ile Val Leu
                740                 745                 750

Asn Thr Leu Phe Met Ala Met Glu His Tyr Pro Met Thr Asp His Phe
            755                 760                 765

Asn Asn Val Leu Thr Val Gly Asn Leu Val Phe Thr Gly Ile Phe Thr
        770                 775                 780

Ala Glu Met Phe Leu Lys Ile Ile Ala Met Asp Pro Tyr Tyr Tyr Phe
785                 790                 795                 800

Gln Glu Gly Trp Asn Ile Phe Asp Gly Phe Ile Val Thr Leu Ser Leu
                805                 810                 815

Val Glu Leu Gly Leu Ala Asn Val Glu Gly Leu Ser Val Leu Arg Ser
                820                 825                 830

Phe Arg Leu Leu Arg Val Phe Lys Leu Ala Lys Ser Trp Pro Thr Leu
            835                 840                 845

Asn Met Leu Ile Lys Ile Ile Gly Asn Ser Val Gly Ala Leu Gly Asn
850                 855                 860

Leu Thr Leu Val Leu Ala Ile Ile Val Phe Ile Phe Ala Val Val Gly
865                 870                 875                 880

Met Gln Leu Phe Gly Lys Ser Tyr Lys Asp Cys Val Cys Lys Ile Ala
                885                 890                 895

Ser Asp Cys Gln Leu Pro Arg Trp His Met Asn Asp Phe Phe His Ser
            900                 905                 910

Phe Leu Ile Val Phe Arg Val Leu Cys Gly Glu Trp Ile Glu Thr Met
        915                 920                 925

Trp Asp Cys Met Glu Val Ala Gly Gln Ala Met Cys Leu Thr Val Phe
930                 935                 940

Met Met Val Met Val Ile Gly Asn Leu Val Val Leu Asn Leu Phe Leu
945                 950                 955                 960

Ala Leu Leu Leu Ser Ser Phe Ser Ala Asp Asn Leu Ala Ala Thr Asp
                965                 970                 975

Asp Asp Asn Glu Met Asn Asn Leu Gln Ile Ala Val Asp Arg Met His
            980                 985                 990

Lys Gly Val Ala Tyr Val Lys Arg Lys Ile Tyr Glu Phe Ile Gln Gln
        995                 1000                1005

Ser Phe Ile Arg Lys Gln Lys Ile Leu Asp Glu Ile Lys Pro Leu
    1010                1015                1020

Asp Asp Leu Asn Asn Lys Lys Asp Ser Cys Met Ser Asn His Thr
    1025                1030                1035
```

```
Ala Glu Ile Gly Lys Asp Leu Asp Tyr Leu Lys Asp Val Asn Gly
1040                1045                1050

Thr Thr Ser Gly Ile Gly Thr Gly Ser Ser Val Glu Lys Tyr Ile
1055                1060                1065

Ile Asp Glu Ser Asp Tyr Met Ser Phe Ile Asn Asn Pro Ser Leu
1070                1075                1080

Thr Val Thr Val Pro Ile Ala Val Gly Glu Ser Asp Phe Glu Asn
1085                1090                1095

Leu Asn Thr Glu Asp Phe Ser Ser Glu Ser Asp Leu Glu Glu Ser
1100                1105                1110

Lys Glu Lys Leu Asn Glu Ser Ser Ser Ser Glu Gly Ser Thr
1115                1120                1125

Val Asp Ile Gly Ala Pro Val Glu Glu Gln Pro Val Val Glu Pro
1130                1135                1140

Glu Glu Thr Leu Glu Pro Glu Ala Cys Phe Thr Glu Gly Cys Val
1145                1150                1155

Gln Arg Phe Lys Cys Cys Gln Ile Asn Val Glu Glu Gly Arg Gly
1160                1165                1170

Lys Gln Trp Trp Asn Leu Arg Arg Thr Cys Phe Arg Ile Val Glu
1175                1180                1185

His Asn Trp Phe Glu Thr Phe Ile Val Phe Met Ile Leu Leu Ser
1190                1195                1200

Ser Gly Ala Leu Ala Phe Glu Asp Ile Tyr Ile Asp Gln Arg Lys
1205                1210                1215

Thr Ile Lys Thr Met Leu Glu Tyr Ala Asp Lys Val Phe Thr Tyr
1220                1225                1230

Ile Phe Ile Leu Glu Met Leu Leu Lys Trp Val Ala Tyr Gly Tyr
1235                1240                1245

Gln Thr Tyr Phe Thr Asn Ala Trp Cys Trp Leu Asp Phe Leu Ile
1250                1255                1260

Val Asp Val Ser Leu Val Ser Leu Thr Ala Asn Ala Leu Gly Tyr
1265                1270                1275

Ser Glu Leu Gly Ala Ile Lys Ser Leu Arg Thr Leu Arg Ala Leu
1280                1285                1290

Arg Pro Leu Arg Ala Leu Ser Arg Phe Glu Gly Met Arg Val Val
1295                1300                1305

Val Asn Ala Leu Leu Gly Ala Ile Pro Ser Ile Met Asn Val Leu
1310                1315                1320

Leu Val Cys Leu Ile Phe Trp Leu Ile Phe Ser Ile Met Gly Val
1325                1330                1335

Asn Leu Phe Ala Gly Lys Phe Tyr His Cys Ile Asn Thr Thr Thr
1340                1345                1350

Gly Asp Arg Phe Asp Ile Glu Asp Val Asn Asn His Thr Asp Cys
1355                1360                1365

Leu Lys Leu Ile Glu Arg Asn Glu Thr Ala Arg Trp Lys Asn Val
1370                1375                1380

Lys Val Asn Phe Asp Asn Val Gly Phe Gly Tyr Leu Ser Leu Leu
1385                1390                1395

Gln Val Ala Thr Phe Lys Gly Trp Met Asp Ile Met Tyr Ala Ala
1400                1405                1410

Val Asp Ser Arg Asn Val Glu Leu Gln Pro Lys Tyr Glu Glu Ser
1415                1420                1425
```

```
Leu Tyr Met Tyr Leu Tyr Phe Val Ile Phe Ile Ile Phe Gly Ser
1430                1435                1440

Phe Phe Thr Leu Asn Leu Phe Ile Gly Val Ile Ile Asp Asn Phe
1445                1450                1455

Asn Gln Gln Lys Lys Lys Phe Gly Gly Gln Asp Ile Phe Met Thr
1460                1465                1470

Glu Glu Gln Lys Lys Tyr Tyr Asn Ala Met Lys Lys Leu Gly Ser
1475                1480                1485

Lys Lys Pro Gln Lys Pro Ile Pro Arg Pro Gly Asn Lys Phe Gln
1490                1495                1500

Gly Met Val Phe Asp Phe Val Thr Arg Gln Val Phe Asp Ile Ser
1505                1510                1515

Ile Met Ile Leu Ile Cys Leu Asn Met Val Thr Met Met Val Glu
1520                1525                1530

Thr Asp Asp Gln Ser Glu Tyr Val Thr Thr Ile Leu Ser Arg Ile
1535                1540                1545

Asn Leu Val Phe Ile Val Leu Phe Thr Gly Glu Cys Val Leu Lys
1550                1555                1560

Leu Ile Ser Leu Arg His Tyr Tyr Phe Thr Ile Gly Trp Asn Ile
1565                1570                1575

Phe Asp Phe Val Val Val Ile Leu Ser Ile Val Gly Met Phe Leu
1580                1585                1590

Ala Glu Leu Ile Glu Lys Tyr Phe Val Ser Pro Thr Leu Phe Arg
1595                1600                1605

Val Ile Arg Leu Ala Arg Ile Gly Arg Ile Leu Arg Leu Ile Lys
1610                1615                1620

Gly Ala Lys Gly Ile Arg Thr Leu Leu Phe Ala Leu Met Met Ser
1625                1630                1635

Leu Pro Ala Leu Phe Asn Ile Gly Leu Leu Leu Phe Leu Val Met
1640                1645                1650

Phe Ile Tyr Ala Ile Phe Gly Met Ser Asn Phe Ala Tyr Val Lys
1655                1660                1665

Arg Glu Val Gly Ile Asp Asp Met Phe Asn Phe Glu Thr Phe Gly
1670                1675                1680

Asn Ser Met Ile Cys Leu Phe Gln Ile Thr Thr Ser Ala Gly Trp
1685                1690                1695

Asp Gly Leu Leu Ala Pro Ile Leu Asn Ser Lys Pro Pro Asp Cys
1700                1705                1710

Asp Pro Asn Lys Val Asn Pro Gly Ser Ser Val Lys Gly Asp Cys
1715                1720                1725

Gly Asn Pro Ser Val Gly Ile Phe Phe Phe Val Ser Tyr Ile Ile
1730                1735                1740

Ile Ser Phe Leu Val Val Val Asn Met Tyr Ile Ala Val Ile Leu
1745                1750                1755

Glu Asn Phe Ser Val Ala Thr Glu Glu Ser Ala Glu Pro Leu Ser
1760                1765                1770

Glu Asp Asp Phe Glu Met Phe Tyr Glu Val Trp Glu Lys Phe Asp
1775                1780                1785

Pro Asp Ala Thr Gln Phe Met Glu Phe Glu Lys Leu Ser Gln Phe
1790                1795                1800

Ala Ala Ala Leu Glu Pro Pro Leu Asn Leu Pro Gln Pro Asn Lys
1805                1810                1815

Leu Gln Leu Ile Ala Met Asp Leu Pro Met Val Ser Gly Asp Arg
```

```
                    1820                1825                1830

Ile His Cys Leu Asp Ile Leu Phe Ala Phe Thr Lys Arg Val Leu
        1835                1840                1845

Gly Glu Ser Gly Glu Met Asp Ala Leu Arg Ile Gln Met Glu Glu
    1850                1855                1860

Arg Phe Met Ala Ser Asn Pro Ser Lys Val Ser Tyr Gln Pro Ile
1865                1870                1875

Thr Thr Thr Leu Lys Arg Lys Gln Glu Glu Val Ser Ala Val Ile
    1880                1885                1890

Ile Gln Arg Ala Tyr Arg Arg His Leu Leu Lys Arg Thr Val Lys
    1895                1900                1905

Gln Ala Ser Phe Thr Tyr Asn Lys Asn Lys Ile Lys Gly Gly Ala
    1910                1915                1920

Asn Leu Leu Ile Lys Glu Asp Met Ile Ile Asp Arg Ile Asn Glu
    1925                1930                1935

Asn Ser Ile Thr Glu Lys Thr Asp Leu Thr Met Ser Thr Ala Ala
    1940                1945                1950

Cys Pro Pro Ser Tyr Asp Arg Val Thr Lys Pro Ile Val Glu Lys
    1955                1960                1965

His Glu Gln Glu Gly Lys Asp Glu Lys Ala Lys Gly Lys
    1970                1975                1980

<210> SEQ ID NO 16
<211> LENGTH: 72
<212> TYPE: DNA
<213> ORGANISM: Artificial Sequence
<220> FEATURE:
<223> OTHER INFORMATION: Synthetic Construct

<400> SEQUENCE: 16
ggtcccatgg tgtaatggtt agcactctgg actttaaatc cagcgatccg agttcaaatc      60
tcggtgggac ct                                                         72

<210> SEQ ID NO 17
<211> LENGTH: 72
<212> TYPE: DNA
<213> ORGANISM: Artificial Sequence
<220> FEATURE:
<223> OTHER INFORMATION: Synthetic Construct

<400> SEQUENCE: 17
ggtcccatgg tgtaatggtt agcactctgg actttaaatc cagcaatccg agttcgaatc      60
tcggtgggac ct                                                         72

<210> SEQ ID NO 18
<211> LENGTH: 72
<212> TYPE: DNA
<213> ORGANISM: Artificial Sequence
<220> FEATURE:
<223> OTHER INFORMATION: Synthetic Construct

<400> SEQUENCE: 18
ggccccatgg tgtaatggtt agcactctgg actttaaatc cagcgatccg agttcaaatc      60
tcggtgggac ct                                                         72

<210> SEQ ID NO 19
<211> LENGTH: 473
<212> TYPE: DNA
<213> ORGANISM: Artificial Sequence
```

```
<220> FEATURE:
<223> OTHER INFORMATION: Synthetic Construct

<400> SEQUENCE: 19
cggaggagcg caggaagaca tgatatcccc gggaccagaa acgccgggaa cacgaaggac      60
gcagaagccc tcgccacgcc gcccgtgggg ccccggtcca gggcccagtc cctcaaacac     120
ggacaccgct gccgctctgg aaaggccgcc cagagccctc ctagcttgag gagactcgcg     180
gccgccttaa gaagccagca ggtcccatgg tgtaatggtt agcactctgg actttaaatc     240
cagcgatccg agttcaaatc tcggtgggac ctcacgagac tttttggtcc tacaattcct     300
gttttggaga ccgcttccgg cagcagccac ctcgggctgt gtgggtagcc tcactgacct     360
ggcctacagc ggcttggggt ccctccccct ctctcaagat gtttcattt cagggccgtt      420 ctggggtgt cagtgcgcac gcgcgagagt cgggcagaaa aataaatgtg ttg            473

<210> SEQ ID NO 20
<211> LENGTH: 472
<212> TYPE: DNA
<213> ORGANISM: Artificial Sequence
<220> FEATURE:
<223> OTHER INFORMATION: Synthetic Construct

<400> SEQUENCE: 20
caaaagcgca ggaaagagtg aagagatctc cctgaattt attttgacag ttactccttc       60
ttcagcagca aagcgtcagc tttcctgtca gcgtgagtct cactgaagcc tgacctaact     120
ctttcggatc ggaactagaa agtttattat caaggaggta tttaaccacg actatactta     180
cctactgtac ccttgtggtt ggtcccatgg tgtaatggtt agcactctgg actttaaatc     240
cagcaatccg agttcgaatc tcggtgggac ctttcaaagg tgaacgtttt acagttcctg     300
gcttggcctc tgaatgtggg aaaaattcgt tcctccgctt cccatcgaat tctcgtcgaa     360
aacaactttg tggtcgcgtg cacggtattg aactctcccc ttctatccaa gcatgaaagt     420
accaagctct ttcgcctaga agaacgcttt caaagcgtat caaattcacg gg            472

<210> SEQ ID NO 21
<211> LENGTH: 472
<212> TYPE: DNA
<213> ORGANISM: Artificial Sequence
<220> FEATURE:
<223> OTHER INFORMATION: Synthetic Construct

<400> SEQUENCE: 21
actcaaacgg gttcaagttt tttcagtttc taagacggac ttggtccaga taggtttgta      60
gtgcatgtga gtctcttgga gcttctgcta catgggatgc agatagtatt aatttaataa     120
atattaagag aatactgcat cgaatagaca tgctctgtaa tcagtatttt tataaattca     180
tgaaattggt ggcggaaggc ggccccatgg tgtaatggtt agcactctgg actttaaatc     240
cagcgatccg agttcaaatc tcggtgggac ctgtcctgct ttttgtgacc catccttcgt     300
tcgtctctta aatcatcaac acacagcgat ctgtggattt actttctcat tcacggtttc     360
ttcttcggat tagcaagtgt catgtaactc ctgactgtca tttctagctt ctgagtagta     420
tcatgtcctt gtacattctt ggtctttct cttagcatcc acacttccct ga              472
```